United States Patent [19]
van Ooyen et al.

[11] Patent Number: 5,171,844
[45] Date of Patent: Dec. 15, 1992

[54] PROTEINS WITH FACTOR VIII ACTIVITY: PROCESS FOR THEIR PREPARATION USING GENETICALLY-ENGINEERED CELLS AND PHARMACEUTICAL COMPOSITIONS CONTAINING THEM

[75] Inventors: Albert J. J. van Ooyen, Voorburg; Hans Pannekoek, Aalsmeer; Martinus P. Verbeet, Amsterdam; Robert W. van Leen, Nijmegen, all of Netherlands

[73] Assignee: Gist-Brocades N.W., Delft, Netherlands

[21] Appl. No.: 205,226

[22] Filed: Jun. 10, 1988

[30] Foreign Application Priority Data

Jun. 12, 1987 [EP] European Pat. Off. ........... 87201121

[51] Int. Cl.$^5$ ................. C07K 13/00; A61K 37/02
[52] U.S. Cl. ................. 530/383; 530/395; 530/830; 514/12; 435/69.6
[58] Field of Search ................. 530/383; 514/2, 8, 12; 435/69.6

[56] References Cited

U.S. PATENT DOCUMENTS 4,868,112  9/1989  Toole .................... 435/68

FOREIGN PATENT DOCUMENTS 0160457  11/1985  European Pat. Off. .
0232112   8/1987  European Pat. Off. .
0253455   1/1988  European Pat. Off. .
0265778   5/1988  European Pat. Off. .
86/06101  10/1986  PCT Int'l Appl. .
87/07144  12/1987  PCT Int'l Appl. .
88/00831   2/1988  PCT Int'l Appl. .

OTHER PUBLICATIONS

Eaton et al. (1986) Prog. Hemostasis and Thrombosis 8, 47–70.

Eaton et al., *Biochemistry*, Construction and Characterization of an Active Factor VIII Variant Lacking the Central One-Third of the Molecule, (1986) 25:8343–8347.

Burke et al., *The Journal of Biological Chemistry*, The Functional Domains of Coagulation Factor VIII:C, (1986) 261:12574–12578.

*Primary Examiner*—Robert A. Wax
*Assistant Examiner*—R. Keith Baker
*Attorney, Agent, or Firm*—Barbara Rae-Venter

[57] ABSTRACT

Novel polypeptides having Factor VIII activity are provided as well as compositions and methods for their preparation. The polypeptides comprise derivatives and fragments of Factor VIII and have sequences substantially similar to portions of naturally occuring Factor VIII. The polypeptides find use in treatment of Hemophilia A.

1 Claim, 12 Drawing Sheets

```
       10         20         30         40         50         60
GTCGACATGCAAATAGAGCTCTCCACCTGCTTCTTTCTGTGCCTTTTGCGATTCTGCTTT
  -19 M  Q  I  E  L  S  T  C  F  F  L  C  L  L  R  F  C  F      -2

70         80         90        100        110        120
AGTGCCACCAGAAGATACTACCTGGGTGCAGTGGAACTGTCATGGGACTATATGCAAAGT
    S  A  T  R  R  Y  Y  L  G  A  V  E  L  S  W  D  Y  M  Q  S  19

130        140        150        160        170        180
GATCTCGGTGAGCTGCCTGTGGACGCAAGATTTCCTCCTAGAGTGCCAAAATCTTTTCCA
    D  L  G  E  L  P  V  D  A  R  F  P  P  R  V  P  K  S  F  P 190        200        210        220        230        240
TTCAACACCTCAGTCGTGTACAAAAAGACTCTGTTTGTAGAATTCACGGATCACCTTTTC
    F  N  T  S  V  V  Y  K  K  T  L  F  V  E  F  T  D  H  L  F  59

250        260        270        280        290        300
AACATCGCTAAGCCAAGGCCACCCTGGATGGGTCTGCTAGGTCCTACCATCCAGGCTGAG
    N  I  A  K  P  R  P  P  W  M  G  L  L  G  P  T  I  Q  A  E 310        320        330        340        350        360
GTTTATGATACAGTGGTCATTACACTTAAGAACATGGCTTCCCATCCTGTCAGTCTTCAT
    V  Y  D  T  V  V  I  T  L  K  N  M  A  S  H  P  V  S  L  H  99

370        380        390        400        410        420
GCTGTTGGTGTATCCTACTGGAAAGCTTCTGAGGGAGCTGAATATGATGATCAGACCAGT
    A  V  G  V  S  Y  W  K  A  S  E  G  A  E  Y  D  D  Q  T  S 430        440        450        460        470        480
CAAAGGGAGAAAGAAGATGATAAAGTCTTCCCTGGTGGAAGCCATACATATGTCTGGCAG
    Q  R  E  K  E  D  D  K  V  F  P  G  G  S  H  T  Y  V  W  Q  139

490        500        510        520        530        540
GTCCTGAAAGAGAATGGTCCAATGGCCTCTGACCCACTGTGCCTTACCTACTCATATCTT
    V  L  K  E  N  G  P  M  A  S  D  P  L  C  L  T  Y  S  Y  L 550        560        570        580        590        600
TCTCATGTGGACCTGGTAAAAGACTTGAATTCAGGCCTCATTGGAGCCCTACTAGTATGT
    S  H  V  D  L  V  K  D  L  N  S  G  L  I  G  A  L  L  V  C  170

610        620        630        640        650        660
AGAGAAGGGAGTCTGGCCAAGGAAAAGACACAGACCTTGCACAAATTTATACTACTTTTT
    R  E  G  S  L  A  K  E  K  T  Q  T  L  H  K  F  I  L  L  F 670        680        690        700        710        720
GCTGTATTTGATGAAGGGAAAAGTTGGCACTCAGAAACAAAGAACTCCTTGATGCAGGAT
    A  V  F  D  E  G  K  S  W  H  S  E  T  K  N  S  L  M  Q  D  219

730        740        750        760        770        780
AGGGATGCTGCATCTGCTCGGGCCTGGCCTAAAATGCACACAGTCAATGGTTATGTAAAC
    R  D  A  A  S  A  R  A  W  P  K  M  H  T  V  N  G  Y  V  N 790        800        810        820        830        840
AGGTCTCTGCCAGGTCTGATTGGATGCCACAGGAAATCAGTCTATTGGCATGTGATTGGA
    R  S  L  P  G  L  I  G  C  H  R  K  S  V  Y  W  H  V  I  G  259

850        860        870        880        890        900
ATGGGCACCACTCCTGAAGTGCACTCAATATTCCTCGAAGGTCACACATTTCTTGTGAGG
    M  G  T  T  P  E  V  H  S  I  F  L  E  G  H  T  F  L  V  R
```

FIG. IA

```
          910       920       930       940       950       960
AACCATCGCCAGGCGTCCTTGGAAATCTCGCCAATAACTTTCCTTACTGCTCAAACACTC
 N  H  R  Q  A  S  L  E  I  S  P  I  T  F  L  T  A  Q  T  L    299

970       980       990      1000      1010      1020
TTGATGGACCTTGGACAGTTTCTACTGTTTTGTCATATCTCTTCCCACCAACATGATGGC
 L  M  D  L  G  Q  F  L  L  F  C  H  I  S  S  H  Q  H  D  G 1030      1040      1050      1060      1070      1080
ATGGAAGCTTATGTCAAAGTAGACAGCTGTCCAGAGGAACCCCAACTACGAATGAAAAAT
 M  E  A  Y  V  K  V  D  S  C  P  E  E  P  Q  L  R  M  K  N    339

1090      1100      1110      1120      1130      1140
AATGAAGAAGCGGAAGACTATGATGATGATCTTACTGATTCTGAAATGGATGTGGTCAGG
 N  E  E  A  E  D  Y  D  D  D  L  T  D  S  E  M  D  V  V  R 1150      1160      1170      1180      1190      1200
TTTGATGATGACAACTCTCCTTCCTTTATCCAAATTCGCTCAGTTGCCAAGAAGCATCCT
 F  D  D  D  N  S  P  S  F  I  Q  I  R  S  V  A  K  K  H  P    379

1210      1220      1230      1240      1250      1260
AAAACTTGGGTACATTACATTGCTGCTGAAGAGGAGGACTGGGACTATGCTCCCTTAGTC
 K  T  W  V  H  Y  I  A  A  E  E  E  D  W  D  Y  A  P  L  V 1270      1280      1290      1300      1310      1320
CTCGCCCCCGATGACAGAAGTTATAAAAGTCAATATTTGAACAATGGCCCTCAGCGGATT
 L  A  P  D  D  R  S  Y  K  S  Q  Y  L  N  N  G  P  Q  R  I    419

1330      1340      1350      1360      1370      1380
GGTAGGAAGTACAAAAAAGTCCGATTTATGGCATACACAGATGAAACCTTTAAGACTCGT
 G  R  K  Y  K  K  V  R  F  M  A  Y  T  D  E  T  F  K  T  R 1390      1400      1410      1420      1430      1440
GAAGCTATTCAGCATGAATCAGGAATCTTGGGACCTTTACTTTATGGGGAAGTTGGAGAC
 E  A  I  Q  H  E  S  G  I  L  G  P  L  L  Y  G  E  V  G  D    459

1450      1460      1470      1480      1490      1500
ACACTGTTGATTATATTTAAGAATCAAGCAAGCAGACCATATAACATCTACCCTCACGGA
 T  L  L  I  I  F  K  N  Q  A  S  R  P  Y  N  I  Y  P  H  G 1510      1520      1530      1540      1550      1560
ATCACTGATGTCCGTCCTTTGTATTCAAGGAGATTACCAAAAGGTGTAAAACATTTGAAG
 I  T  D  V  R  P  L  Y  S  R  R  L  P  K  G  V  K  H  L  K    499

1570      1580      1590      1600      1610      1620
GATTTTCCAATTCTGCCAGGAGAAATATTCAAATATAAATGGACAGTGACTGTAGAAGAT
 D  F  P  I  L  P  G  E  I  F  K  Y  K  W  T  V  T  V  E  D 1630      1640      1650      1660      1670      1680
GGGCCAACTAAATCAGATCCTCGGTGCCTGACCCGCTATTACTCTAGTTTCGTTAATATG
 G  P  T  K  S  D  P  R  C  L  T  R  Y  Y  S  S  F  V  N  M    539

1690      1700      1710      1720      1730      1740
GAGAGAGATCTAGCTTCAGGACTCATTGGCCCTCTCCTCATCTGCTACAAAGAATCTGTA
 E  R  D  L  A  S  G  L  I  G  P  L  L  I  C  Y  K  E  S  V 1750      1760      1770      1780      1790      1800
GATCAAAGAGGAAACCAGATAATGTCAGACAAGAGGAATGTCATCCTGTTTTCTGTATTT
 D  Q  R  G  N  Q  I  M  S  D  K  R  N  V  I  L  F  S  V  F    579
```

FIG. 1B

```
         1810      1820      1830      1840      1850      1860
GATGAGAACCGAAGCTGGTACCTCACAGAGAATATACAACGCTTTCTCCCCAATCCAGCT
 D  E  N  R  S  W  Y  L  T  E  N  I  Q  R  F  L  P  N  P  A 1870      1880      1890      1900      1910      1920
GGAGTGCAGCTTGAGGATCCAGAGTTCCAAGCCTCCAACATCATGCACAGCATCAATGGC
 G  V  Q  L  E  D  P  E  F  Q  A  S  N  I  M  H  S  I  N  G    619

1930      1940      1950      1960      1970      1980
TATGTTTTTGATAGTTTGCAGTTGTCAGTTTGTTTGCATGAGGTGGCATACTGGTACATT
 Y  V  F  D  S  L  Q  L  S  V  C  L  H  E  V  A  Y  W  Y  I 1990      2000      2010      2020      2030      2040
CTAAGCATTGGAGCACAGACTGACTTCCTTTCTGTCTTCTTCTCTGGATATACCTTCAAA
 L  S  I  G  A  Q  T  D  F  L  S  V  F  F  S  G  Y  T  F  K    659

2050      2060      2070      2080      2090      2100
CACAAAATGGTCTATGAAGACACACTCACCCTATTCCCATTCTCAGGAGAAACTGTCTTC
 H  K  M  V  Y  E  D  T  L  T  L  F  P  F  S  G  E  T  V  F 2110      2120      2130      2140      2150      2160
ATGTCGATGGAAAACCCAGGTCTATGGATTCTGGGGTGCCACAACTCAGACTTTCGGAAC
 M  S  M  E  N  P  G  L  W  I  L  G  C  H  N  S  D  F  R  N    699

2170      2180      2190      2200      2210      2220
AGAGGCATGACCGCCTTACTGAAGGTTTCTAGTTGTGACAAGAACACTGGTGATTATTAC
 R  G  M  T  A  L  L  K  V  S  S  C  D  K  N  T  G  D  Y  Y
                                      12

2230      2240      2250      2260      2270      2280
GAGGACAGTTATGAAGATATTTCAGCATACTTGCTGAGTAAAAACAATGCCATTGAACCA
 E  D  S  Y  E  D  I  S  A  Y  L  L  S  K  N  N  A  I  E  P    739

2290      2300      2310      2320      2330      2340
AGAAGCTTCTCCCAGAATTCAAGACACCCTAGCACTAGGCAAAAGCAATTTAATGCCACC
 R  S  F  S  Q  N  S  R  H  P  S  T  R  Q  K  Q  F  N  A  T 2350      2360      2370      2380      2390      2400
ACAATTCCAGAAAATGACATAGAGAAGACTGACCCTTGGTTTGCACACAGAACACCTATG
 T  I  P  E  N  D  I  E  K  T  D  P  W  F  A  H  R  T  P  M    779

2410      2420      2430      2440      2450      2460
CCTAAAATACAAAATGTCTCCTCTAGTGATTTGTTGATGCTCTTGCGACAGAGTCCTACT
 P  K  I  Q  N  V  S  S  S  D  L  L  M  L  L  R  Q  S  P  T 2470      2480      2490      2500      2510      2520
CCACATGGGCTATCCTTATCTGATCTCCAAGAAGCCAAATATGAGACTTTTTCTGATGAT
 P  H  G  L  S  L  S  D  L  Q  E  A  K  Y  E  T  F  S  D  D    819

2530      2540      2550      2560      2570      2580
CCATCACCTGGAGCAATAGACAGTAATAACAGCCTGTCTGAAATGACACACTTCAGGCCA
 P  S  P  G  A  I  D  S  N  N  S  L  S  E  M  T  H  F  R  P 2590      2600      2610      2620      2630      2640
CAGCTCCATCACAGTGGGGACATGGTATTTACCCCTGAGTCAGGCCTCCAATTAAGATTA
 Q  L  H  H  S  G  D  M  V  F  T  P  E  S  G  L  Q  L  R  L    859

2650      2660      2670      2680      2690      2700
AATGAGAAACTGGGGACAACTGCAGCAACAGAGTTGAAGAAACTTGATTTCAAAGTTTCT
 N  E  K  L  G  T  T  A  A  T  E  L  K  K  L  D  F  K  V  S
```

FIG. IC

```
       2710      2720      2730      2740      2750      2760
AGTACATCAAATAATCTGATTTCAACAATTCCATCAGACAATTTGGCAGCAGGTACTGAT
 S  T  S  N  N  L  I  S  T  I  P  S  D  N  L  A  A  G  T  D     899

2770      2780      2790      2800      2810      2820
AATACAAGTTCCTTAGGACCCCCAAGTATGCCAGTTCATTATGATAGTCAATTAGATACC
 N  T  S  S  L  G  P  P  S  M  P  V  H  Y  D  S  Q  L  D  T 2830      2840      2850      2860      2870      2880
ACTCTATTTGGCAAAAAGTCATCTCCCCTTACTGAGTCTGGTGGACCTCTGAGCTTGAGT
 T  L  F  G  K  K  S  S  P  L  T  E  S  G  G  P  L  S  L  S    939

2890      2900      2910      2920      2930      2940
GAAGAAAATAATGATTCAAAGTTGTTAGAATCAGGTTTAATGAATAGCCAAGAAAGTTCA
 E  E  N  N  D  S  K  L  L  E  S  G  L  M  N  S  Q  E  S  S 2950      2960      2970      2980      2990      3000
TGGGGAAAAAATGTATCGTCAACAGAGAGTGGTAGGTTATTCAAAGGGAAAAGAGCTCAT
 W  G  K  N  V  S  S  T  E  S  G  R  L  F  K  G  K  R  A  H    979

3010      3020      3030      3040      3050      3060
GGACCTGCTTTGTTGACTAAAGATAATGCCTTATTCAAAGTTAGCATCTCTTTGTTAAAG
 G  P  A  L  L  T  K  D  N  A  L  F  K  V  S  I  S  L  L  K 3070      3080      3090      3100      3110      3120
ACAAACAAAACTTCCAATAATTCAGCAACTAATAGAAAGACTCACATTGATGGCCCATCA
 T  N  K  T  S  N  N  S  A  T  N  R  K  T  H  I  D  G  P  S   1019

3130      3140      3150      3160      3170      3180
TTATTAATTGAGAATAGTCCATCAGTCTGGCAAAATATATTAGAAAGTGACACTGAGTTT
 L  L  I  E  N  S  P  S  V  W  Q  N  I  L  E  S  D  T  E  F 3190      3200      3210      3220      3230      3240
AAAAAGTGACACCTTTGATTCATGACAGAATGCTTATGGACAAAAATGCTACAGCTTTG
 K  K  V  T  P  L  I  H  D  R  M  L  M  D  K  N  A  T  A  L   1059

3250      3260      3270      3280      3290      3300
AGGCTAAATCATATGTCAAATAAAACTACTTCATCAAAAAACATGGAAATGGTCCAACAG
 R  L  N  H  M  S  N  K  T  T  S  S  K  N  M  E  M  V  Q  Q 3310      3320      3330      3340      3350      3360
AAAAAAGAGGGCCCCATTCCACCAGATGCACAAAATCCAGATATGTCGTTCTTTAAGATG
 K  K  E  G  P  I  P  P  D  A  Q  N  P  D  M  S  F  F  K  M   1099

3370      3380      3390      3400      3410      3420
CTATTCTTGCCAGAATCAGCAAGGTGGATACAAAGGACTCATGGAAAGAACTCTCTGAAC
 L  F  L  P  E  S  A  R  W  I  Q  R  T  H  G  K  N  S  L  N 3430      3440      3450      3460      3470      3480
TCTGGGCAAGGCCCCAGTCCAAAGCAATTAGTATCCTTAGGACCAGAAAAATCTGTGGAA
 S  G  Q  G  P  S  P  K  Q  L  V  S  L  G  P  E  K  S  V  E   1139

3490      3500      3510      3520      3530      3540
GGTCAGAATTTCTTGTCTGAGAAAAACAAAGTGGTAGTAGGAAAGGGTGAATTTACAAAG
 G  Q  N  F  L  S  E  K  N  K  V  V  V  G  K  G  E  F  T  K 3550      3560      3570      3580      3590      3600
GACGTAGGACTCAAAGAGATGGTTTTTCCAAGCAGCAGAAACCTATTTCTTACTAACTTG
 D  V  G  L  K  E  M  V  F  P  S  S  R  N  L  F  L  T  N  L   1179
```

FIG. ID

```
          3610      3620      3630      3640      3650      3660
GATAATTTACATGAAAATAATACACACAATCAAGAAAAAAAAATTCAGGAAGAAATAGAA
  D  N  L  H  E  N  N  T  H  N  Q  E  K  K  I  Q  E  E  I  E 3670      3680      3690      3700      3710      3720
AAGAAGGAAACATTAATCCAAGAGAATGTAGTTTTGCCTCAGATACATACAGTGACTGGC
  K  K  E  T  L  I  Q  E  N  V  V  L  P  Q  I  H  T  V  T  G      1219

3730      3740      3750      3760      3770      3780
ACTAAGAATTTCATGAAGAACCTTTTCTTACTGAGCACTAGGCAAAATGTAGAAGGTTCA
  T  K  N  F  M  K  N  L  F  L  L  S  T  R  Q  N  V  E  G  S 3790      3800      3810      3820      3830      3840
TATGACGGGGCATATGCTCCAGTACTTCAAGATTTTAGGTCATTAAATGATTCAACAAAT
  Y  D  G  A  Y  A  P  V  L  Q  D  F  R  S  L  N  D  S  T  N      1259

3850      3850      3870      3880      3890      3900
AGAACAAAGAAACACACAGCTCATTTCTCAAAAAAGGGGAGGAAGAAAACTTGGAAGGC
  R  T  K  K  H  T  A  H  F  S  K  K  G  E  E  E  N  L  E  G 3910      3920      3930      3940      3950      3960
TTGGGAAATCAAACCAAGCAAATTGTAGAGAAATATGCATGCACCACAAGGATATCTCCT
  L  G  N  Q  T  K  Q  I  V  E  K  Y  A  C  T  T  R  I  S  P      1299

3970      3980      3990      4000      4010      4020
AATACAAGCCAGCAGAATTTTGTCACGCAACGTAGTAAGAGAGCTTTGAAACAATTCAGA
  N  T  S  Q  Q  N  F  V  T  Q  R  S  K  R  A  L  K  Q  F  R 4030      4040      4050      4060      4070      4080
CTCCCACTAGAAGAAACAGAACTTGAAAAAAGGATAATTGTGGATGACACCTCAACCCAG
  L  P  L  E  E  T  E  L  E  K  R  I  I  V  D  D  T  S  T  Q      1339

4090      4100      4110      4120      4130      4140
TGGTCCAAAAACATGAAACATTTGACCCCGAGCACCCTCACACAGATAGACTACAATGAG
  W  S  K  N  M  K  H  L  T  P  S  T  L  T  Q  I  D  Y  N  E 4150      4160      4170      4180      4190      4200
AAGGAGAAAGGGGCCATTACTCAGTCTCCCTTATCAGATTGCCTTACGAGGAGTCATAGC
  K  E  K  G  A  I  T  Q  S  P  L  S  D  C  L  T  R  S  H  S      1379

4210      4220      4230      4240      4250      4260
ATCCCTCAAGCAAATAGATCTCCATTACCCATTGCAAAGGTATCATCATTTCCATCTATT
  I  P  Q  A  N  R  S  P  L  P  I  A  K  V  S  S  F  P  S  I 4270      4280      4290      4300      4310      4320
AGACCTATATATCTGACCAGGGTCCTATTCCAAGACAACTCTTCTCATCTTCCAGCAGCA
  R  P  I  Y  L  T  R  V  L  F  Q  D  N  S  S  H  L  P  A  A      1419

4330      4340      4350      4360      4370      4380
TCTTATAGAAAGAAAGATTCTGGGGTCCAAGAAAGCAGTCATTTCTTACAAGGAGCCAAA
  S  Y  R  K  K  D  S  G  V  Q  E  S  S  H  F  L  Q  G  A  K 4390      4400      4410      4420      4430      4440
AAAAATAACCTTTCTTTAGCCATTCTAACCTTGGAGATGACTGGTGATCAAAGAGAGGTT
  K  N  N  L  S  L  A  I  L  T  L  E  M  T  G  D  Q  R  E  V      1459

4450      4460      4470      4480      4490      4500
GGCTCCCTGGGGACAAGTGCCACAAATTCAGTCACATACAAGAAAGTTGAGAACACTGTT
  G  S  L  G  T  S  A  T  N  S  V  T  Y  K  K  V  E  N  T  V
```

FIG.1E

```
       4510      4520      4530      4540      4550      4560
CTCCCGAAACCAGACTTGCCCAAAACATCTGGCAAAGTTGAATTGCTTCCAAAAGTTCAC
  L  P  K  P  D  L  P  K  T  S  G  K  V  E  L  L  P  K  V  H    1499
       4570      4580      4590      4600      4610      4620
ATTTATCAGAAGGACCTATTCCCTACGGAAACTAGCAATGGGTCTCCTGGCCATCTGGAT
  I  Y  Q  K  D  L  F  P  T  E  T  S  N  G  S  P  G  H  L  D
       4630      4640      4650      4660      4670      4680
CTCGTGGAAGGGAGCCTTCTTCAGGGAACAGAGGGAGCGATTAAGTGGAATGAAGCAAAC
  L  V  E  G  S  L  L  Q  G  T  E  G  A  I  K  W  N  E  A  N   1539
       4690      4700      4710      4720      4730      4740
AGACCTGGAAAAGTTCCCTTTCTGAGAGTAGCAACAGAAAGCTCTGCAAAGACTCCCTCC
  R  P  G  K  V  P  F  L  R  V  A  T  E  S  S  A  K  T  P  S
       4750      4760      4770      4780      4790      4800
AAGCTATTGGATCCTCTTGCTTGGGATAACCACTATGGTACTCAGATACCAAAAGAAGAG
  K  L  L  D  P  L  A  W  D  N  H  Y  G  T  Q  I  P  K  E  E   1579
       4810      4820      4830      4840      4850      4860
TGGAAATCCCAAGAGAAGTCACCAGAAAAAACAGCTTTTAAGAAAAAGGATACCATTTTG
  W  K  S  Q  E  K  S  P  E  K  T  A  F  K  K  K  D  T  I  L
       4870      4880      4890      4900      4910      4920
TCCCTGAACGCTTGTGAAAGCAATCATGCAATAGCAGCAATAAATGAGGGACAAAATAAG
  S  L  N  A  C  E  S  N  H  A  I  A  A  I  N  E  G  Q  N  K   1619
       4930      4940      4950      4960      4970      4980
CCCGAAATAGAAGTCACCTGGGCAAAGCAAGGTAGGACTGAAAGGCTGTGCTCTCAAAAC
  P  E  I  E  V  T  W  A  K  Q  G  R  T  E  R  L  C  S  Q  N
                                                      37 38
       4990      5000      5010      5020      5030      5040
CCACCAGTCTTGAAACGCCATCAACGGGAAATAACTCGTACTACTCTTCAGTCAGATCAA
  P  P  V  L  K  R  H  Q  R  E  I  T  R  T  T  L  Q  S  D  Q   1659
                              49
       5050      5060      5070      5080      5090      5100
GAGGAAATTGACTATGATGATACCATATCAGTTGAAATGAAGAAGGAAGATTTTGACATT
  E  E  I  D  Y  D  D  T  I  S  V  E  M  K  K  E  D  F  D  I
       5110      5120      5130      5140      5150      5160
TATGATGAGGATGAAAATCAGAGCCCCCGCAGCTTTCAAAAGAAAACACGACACTATTTT
  Y  D  E  D  E  N  Q  S  P  R  S  F  Q  K  K  T  R  H  Y  F   1699
                                 89 90
       5170      5180      5190      5200      5210      5220
ATTGCTGCAGTGGAGAGGCTCTGGGATTATGGGATGAGTAGCTCCCCACATGTTCTAAGA
  I  A  A  V  E  R  L  W  D  Y  G  M  S  S  S  P  H  V  L  R
       5230      5240      5250      5260      5270      5280
AACAGGGCTCAGAGTGGCAGTGTCCCTCAGTTCAAGAAAGTTGTTTTCCAGGAATTTACT
  N  R  A  Q  S  G  S  V  P  Q  F  K  K  V  V  F  Q  E  F  T   1739
       5290      5300      5310      5320      5330      5340
GATGGCTCCTTTACTCAGCCCTTATACCGTGGAGAACTAAATGAACATTTGGGACTCCTG
  D  G  S  F  T  Q  P  L  Y  R  G  E  L  N  E  H  L  G  L  L
       5350      5360      5370      5380      5390      5400
GGGCCATATATAAGAGCAGAAGTTGAAGATAATATCATGGTAACTTTCAGAAATCAGGCC
  G  P  Y  I  R  A  E  V  E  D  N  I  M  V  T  F  R  N  Q  A   1779
```

FIG. IF

```
       5410      5420      5430      5440      5450      5460
TCTCGTCCCTATTCCTTCTATTCTAGCCTTATTTCTTATGAGGAAGATCAGAGGCAAGGA
 S  R  P  Y  S  F  Y  S  S  L  I  S  Y  E  E  D  Q  R  Q  G 5470      5480      5490      5500      5510      5520
GCAGAACCTAGAAAAAACTTTGTCAAGCCTAATGAAACCAAAACTTACTTTTGGAAAGTG
 A  E  P  R  K  N  F  V  K  P  N  E  T  K  T  Y  F  W  K  V   1819

5530      5540      5550      5560      5570      5580
CAACATCATATGGCACCCACTAAAGATGAGTTTGACTGCAAAGCCTGGGCTTATTTCTCT
 Q  H  H  M  A  P  T  K  D  E  F  D  C  K  A  W  A  Y  F  S 5590      5600      5610      5620      5630      5640
GATGTTGACCTGGAAAAAGATGTGCACTCAGGCCTGATTGGACCCCTTCTGGTCTGCCAC
 D  V  D  L  E  K  D  V  H  S  G  L  I  G  P  L  L  V  C  H   1859

5650      5660      5670      5680      5690      5700
ACTAACACACTGAACCCTGCTCATGGGAGACAAGTGACAGTACAGGAATTTGCTCTGTTT
 T  N  T  L  N  P  A  H  G  R  Q  V  T  V  Q  E  F  A  L  F 5710      5720      5730      5740      5750      5760
TTCACCATCTTTGATGAGACCAAAAGCTGGTACTTCACTGAAAATATGGAAAGAAACTGC
 F  T  I  F  D  E  T  K  S  W  Y  F  T  E  N  M  E  R  N  C   1899

5770      5780      5790      5800      5810      5820
AGGGCTCCCTGCAATATCCAGATGGAAGATCCCACTTTTAAAGAGAATTATCGCTTCCAT
 R  A  P  C  N  I  Q  M  E  D  P  T  F  K  E  N  Y  R  F  H 5830      5840      5850      5860      5870      5880
GCAATCAATGGCTACATAATGGATACACTACCTGGCTTAGTAATGGCTCAGGATCAAAGG
 A  I  N  G  Y  I  M  D  T  L  P  G  L  V  M  A  Q  D  Q  R   1939

5890      5900      5910      5920      5930      5940
ATTCGATGGTATCTGCTCAGCATGGGCAGCAATGAAAACATCCATTCTATTCATTTCAGT
 I  R  W  Y  L  L  S  M  G  S  N  E  N  I  H  S  I  H  F  S 5950      5960      5970      5980      5990      6000
GGACATGTGTTCACTGTACGAAAAAAAGAGGAGTATAAAATGGCACTGTACAATCTCTAT
 G  H  V  F  T  V  R  K  K  E  E  Y  K  M  A  L  Y  N  L  Y   1979

6010      6020      6030      6040      6050      6060
CCAGGTGTTTTTGAGACAGTGGAAATGTTACCATCCAAAGCTGGAATTTGGCGGGTGGAA
 P  G  V  F  E  T  V  E  M  L  P  S  K  A  G  I  W  R  V  E 6070      6080      6090      6100      6110      6120
TGCCTTATTGGCGAGCATCTACATGCTGGGATGAGCACACTTTTTCTGGTGTACAGCAAT
 C  L  I  G  E  H  L  H  A  G  M  S  T  L  F  L  V  Y  S  N   2019

6130      6140      6150      6160      6170      6180
AAGTGTCAGACTCCCCTGGGAATGGCTTCTGGACACATTAGAGATTTTCAGATTACAGCT
 K  C  Q  T  P  L  G  M  A  S  G  H  I  R  D  F  Q  I  T  A 6190      6200      6210      6220      6230      6240
TCAGGACAATATGGACAGTGGGCCCCAAAAGCTGGCCAGACTTCATTATTCCGGATCAATC
 S  G  Q  Y  G  Q  W  A  P  K  L  A  R  L  H  Y  S  G  S  I   2059

6250      6260      6270      6280      6290      6300
AATGCCTGGAGCACCAAGGAGCCCTTTTCTTGGATCAAGGTGGATCTGTTGGCACCAATG
 N  A  W  S  T  K  E  P  F  S  W  I  K  V  D  L  L  A  P  M
```

FIG. IG

```
      6310      6320      6330      6340      6350      6360
ATTATTCACGGCATCAAGACCCAGGGTGCCCGTCAGAAGTTCTCCAGCCTCTACATCTCT
 I  I  H  G  I  K  T  Q  G  A  R  Q  K  F  S  S  L  Y  I  S   2099
      6370      6380      6390      6400      6410      6420
CAGTTTATCATCATGTATAGTCTTGATGGGAAGAAGTGGCAGACTTATCGAGGAAATTCC
 Q  F  I  I  M  Y  S  L  D  G  K  K  W  Q  T  Y  R  G  N  S
      6430      6440      6450      6460      6470      6480
ACTGGAACCTTAATGGTCTTCTTTGGCAATGTGGATTCATCTGGGATAAAACACAATATT
 T  G  T  L  M  V  F  F  G  N  V  D  S  S  G  I  K  H  N  I   2139
      6490      6500      6510      6520      6530      6540
TTTAACCCTCCAATTATTGCTCGATACATCCGTTTGCACCCAACTCATTATAGCATTCGC
 F  N  P  P  I  I  A  R  Y  I  R  L  H  P  T  H  Y  S  I  R
      6550      6560      6570      6580      6590      6600
AGCACTCTTCGCATGGAGTGGATGGGCTGTGATTTAAATAGTTGCAGCATGCCATTGGGA
 S  T  L  R  M  E  W  M  G  C  D  L  N  S  C  S  M  P  L  G   2179
      6610      6620      6630      6640      6650      6660
ATGGAGAGTAAAGCAATATCAGATGCACAGATTACTGCTTCATCCTACTTTACCAATATG
 M  E  S  K  A  I  S  D  A  Q  I  T  A  S  S  Y  F  T  N  M
      6670      6680      6690      6700      6710      6720
TTTGCCACCTGGTCTCCTTCAAAAGCTCGACTTCACCTCCAAGGGAGGAGTAATGCCTGG
 F  A  T  W  S  P  S  K  A  R  L  H  L  Q  G  R  S  N  A  W   2219
      6730      6740      6750      6760      6770      6780
AGACCTCAGGTGAATAATCCAAAAGAGTGGCTGCAAGTGGACTTCCAGAAGACAATGAAA
 R  P  Q  V  N  N  P  K  E  W  L  Q  V  D  F  Q  K  T  M  K
      6790      6800      6810      6820      6830      6840
GTCACAGGAGTAACTACTCAGGGAGTAAAATCTCTGCTTACCAGCATGTATGTGAAGGAG
 V  T  G  V  T  T  Q  G  V  K  S  L  L  T  S  M  Y  V  K  E   2259
      6850      6860      6870      6880      6890      6900
TTCCTCATCTCCAGCAGTCAAGATGGCCATCAGTGGACTCTCTTTTTTCAGAATGGCAAA
 F  L  I  S  S  S  Q  D  G  H  Q  W  T  L  F  F  Q  N  G  K
      6910      6920      6930      6940      6950      6960
GTAAAGGTTTTTCAGGGAAATCAAGACTCCTTCACACCTGTGGTGAACTCTCTAGACCCA
 V  K  V  F  Q  G  N  Q  D  S  F  T  P  V  V  N  S  L  D  P   2299
      6970      6980      6990      7000      7010      7020
CCGTTACTGACTCGCTACCTTCGAATTCACCCCCAGAGTTGGGTGCACCAGATTGCCCTG
 P  L  L  T  R  Y  L  R  I  H  P  Q  S  W  V  H  Q  I  A  L
      7030      7040      7050      7060      7070      7080
AGGATGGAGGTTCTGGGCTGCGAGGCACAGGACCTCTACTGAGGGTGGCCACTGCAGCAC
 R  M  E  V  L  G  C  E  A  Q  D  L  Y
                                        2332 STOP
      7090      7100      7110      7120      7130      7140
CTGCCACTGCCGTCACCTCTCCCTCCTCAGCTCCAGGGCAGTGTCCCTCCCTGGCTTGCC
      7150      7160      7170      7180      7190      7200
TTCTACCTTTGTGCTAAATCCTAGCAGACACTGCCTTGAAGCCTCCTGAATTAACTATCA
      7210      7220      7230      7240      7250      7260
TCAGTCCTGCATTTCTTTGGTGGGGGGCCAGGAGGGTGCATCCAATTTAACTTAACTCTT
```

FIG.IH

```
     7270      7280      7290      7300      7310      7320
ACCTATTTTCTGCAGCTGCTCCCAGATTACTCCTTCCTTCCAATATAACTAGGCAAAAAG
     7330      7340      7350      7360      7370      7380
AAGTGAGGAGAAACCTGCATGAAAGCATTCTTCCCTGAAAAGTTAGGCCTCTCAGAGTCA
     7390      7400      7410      7420      7430      7440
CCACTTCCTCTGTTGTAGAAAAACTATGTGATGAAACTTTGAAAAGATATTTATGATGT
     7450      7460      7470      7480      7490      7500
TAACATTTCAGGTTAAGCCTCATACGTTTAAAATAAAACTCTCAGTTGTTTATTATCCTG
     7510      7520      7530      7540      7550      7560
ATCAAGCATGGAACAAAGCATGTTTCAGGATCAGATCAATACAATCTTGGAGTCAAAAGG
     7570      7580      7590      7600      7610      7620
CAAATCATTTGGACAATCTGCAAAATGGAGAGAATACAATAACTACTACAGTAAAGTCTG
     7630      7640      7650      7660      7670      7680
TTTCTGCTTCCTTACACATAGATATAATTATGTTATTTAGTCATTATGAGGGGCACATTC
     7690      7700      7710      7720      7730      7740
TTATCTCCAAAACTAGCATTCTTAAACTGAGAATTATAGATGGGGTTCAAGAATCCCTAA
     7750      7760      7770      7780      7790      7800
GTCCCCTGAAATTATATAAGGCATTCTGTATAAATGCAAATGTGCATTTTTCTGACGAGT
     7810      7820      7830      7840      7850      7860
GTCCATAGATAAAAAGCCATTTGGTCTTAATTCTGACCAATAAAAAAATAAGTCAGGAGG
     7870      7880      7890      7900      7910      7920
ATGCAATTGTTGAAAGCTTTGAAATAAAATAACAATGTCTTCTTGAAATTTGTGATGGCC
     7930      7940      7950      7960      7970      7980
AAGAAAGAAAATGATGATGACATTAGGCTTCTAAAGGACATACATTTAATATTTCTGTGG
     7990      8000      8010      8020      8030      8040
AAATATGAGGAAAATCCATGGTTATCTGAGATAGGAGATACAAACTTTGTAATTCTAATA
     8050      8060      8070      8080      8090      8100
ATGCACTCAGTTTACTCTCTCCCTCTACTAATTTCCTGCTGAAAATAACACAACAAAAAT
     8110      8120      8130      8140      8150      8160
GTAACAGGGGAAATTATATACCGTGACTGAAAACTAGAGTCCTACTTACATAGTTGAAAT
     8170      8180      8190      8200      8210      8220
ATCAAGGAGGTCAGAAGAAAATTGGACTGGTGAAAACAGAAAAAACACTCCAGTCTGCCA
     8230      8240
TATCACCACACAATAGGATCC
```

PROTEINS WITH FACTOR VIII ACTIVITY: PROCESS FOR THEIR PREPARATION USING GENETICALLY-ENGINEERED CELLS AND PHARMACEUTICAL COMPOSITIONS CONTAINING THEM

INTRODUCTION

1. Technical Field

The invention relates to novel proteins having Factor VIII activity and methods for their preparation using genetically engineered cell-lines and microorganisms.

2. Background

Hemophilia A is a sex-linked bleeding disorder characterized by a deficiency in Factor VIII, an essential element in the blood coagulation cascade. The disease occurs in about 0.01% of the male population. Hemophilia A can be treated by administering Factor VIII-containing blood plasma obtained from healthy donors. This treatment has several disadvantages however. The supply of Factor VIII is limited and very expensive; the concentration of Factor VIII in blood is only about 100 ng/ml and the yields using current plasma fractionation methods are low. Since the source of Factor VIII is pooled donor blood, the recipient runs a high risk of acquiring various infectious diseases, including those caused by hepatitis non-A, non-B, hepatitis B or AIDS viruses which may be present in the donor blood. In addition, recipients may develop antibodies against the exogenous Factor VIII, which can greatly reduce its effectiveness.

Factor VIII comprises three regions, an N-terminal region, the so-called "A1A2-domain"; a central region, the so-called "B domain"; and a C-terminal region comprising the A3, C1 and C2 domains. The A1A2-domain and the C-terminal region are believed essential for clotting activity. Factor VIII circulates in the blood combined with a protein, the von Willebrand factor (vWf), which is believed to protect the sensitive Factor VIII against early degradation.

Factor VIII is obtained in unsatisfactorily low yields when produced by known recombinant DNA processes. Moreover the proteins appear not to be present as an intact chain, hence products are difficult to isolate and to purify and consequently the costs are high. It is therefore desirable to develop an efficient way to produce large quantities of compounds having Factor VIII activity, the compounds preferably having decreased immunogenic activity.

RELEVANT LITERATURE

Molecular cloning of Factor VIII cDNA obtained from human mRNA and the subsequent production of proteins with Factor VIII activity in mammalian, yeast and bacterial cells has been reported. See WO 85/01961, EP 160457, EP 150735, EP 0253455. A method for producing proteins with Factor VIII activity using transformed microorganisms is disclosed in EP 0253455. European patent applications EP 150735 and EP 123945 and Brinkhous et al., *Proc. Natl. Acad. Sci. USA* (1985) 82:8752–8756 disclose Factor VIII activity in proteolytic cleavage products of Factor VIII. A complex of two proteolytic cleavage products of Factor VIII, a 92 kDa and an 80 kDa polypeptide, exhibits enhanced Factor VIII activity. (Fay et al., *Biochem. Biophys. Acta* (1986) 871:268–278; Eaton et al., *Biochemistry* (1986) 25:505–512).

Eaton et al., *Biochemistry* (1986) 25:8343–8347 disclose that a polypeptide in which 766 amino acids (797 through 1562) have been deleted from the central region retains Factor VIII activity. Moreover, mammalian cells transformed with a vector comprising DNA encoding this deletion polypeptide had a higher production level than cells transformed with a vector comprising DNA encoding the full length polypeptide.

PCT application WO 86/06101 discloses that recombinant Factor VIII proteins with deletions of up to 880 amino acids in the central region exhibit Factor VIII activity. The largest deletion stretches from T-760 through N-1639 (numbering according to FIG. 1). The host cells for preparation of the recombinant Factor VIII included mammalian cells, for example Chinese hamster ovary cells.

SUMMARY OF THE INVENTION

Novel compositions, together with expression vectors and methods for their preparation, are provided which comprise derivatives and fragments of Factor VIII. The compositions are prepared by transforming a host cell, preferably a mammalian cell, with an expression vector comprising a DNA sequence encoding a Factor VIII congener, growing the transformed host cell to express the exogenous DNA sequence, and recovering the resultant Factor VIII derivative or fragment from a cell lysate or from conditioned growth medium. The compositions may have enhanced Factor VIII activity and/or decreased immunogenicity. Uses of the compositions include treatment of Hemophilia A.

BRIEF DESCRIPTION OF THE DRAWINGS

FIGS. 1(A)–1(I) show the Factor VIII cDNA insert of pCLB89 including the amino acid sequence A-1 through Y-2332 of Factor VIII and its signal sequence M(-19) through S(-1) with the corresponding sequence of nucleotides. F-973 is encoded by the codon TTC.

FIGS. 3(a–g) show vectors for transient expression of deletion mutant Factor VIII proteins:

a. The landmarks of the pSV2-derived vector: two tandemly situated promoters: the SV40 early transcription promoter (SVep) and the Rous Sarcoma Virus-Long Terminal Repeat (RSV-LTR); the capping site (cap site) and 5' end of the messenger RNA (mRNA); the cDNA insert bearing the full-length Factor VIII coding region with the start codon (ATG), the open reading frame and the stop codon (TGA); the 3' non-coding region of the mRNA with a short intron and the polyadenylation signal (polyA) derived from SV40 DNA (compare to FIG. 2).

b. The 7440 bp (base pairs) fragment SalI-HpaI bearing the full-length Factor VIII coding cDNA is depicted. The start and stop codons of the reading frame are indicated. Restriction endonuclease sites within the full-length cDNA involved in the mutagenesis for the construction of pCLB202 and pCLB203 are shown.

c. Map of the Factor VIII protein. The 19 amino acid long signal peptide and the domain or repeat structure of plasma Factor VIII are shown. A1, A2 and A3 are homologous amino acid sequences. B is a unique region, whereas C1 and C2 are again homologous (Vehar et al., Nature (1984) 312:337-342). The amino acid positions bordering the A and C repeats are given. Below the map the cleavage sites of the proteolytic enzymes, that process Factor VIII, i.e., activated protein C (APC), thrombin (IIa), activated coagulation factor X (Xa), and a trypsin-like protease (indicated with "?") are indicated by arrows. Factor Xa is thought to cleave the IIa- and APC-cleavage sites also shown (Eaton et al., Biochemistry (1986) 25:8343-8347; Fay et al., Biochem. Biophys. Acta (1986) 871:268-278). Their cleavage sites are given. The B region contains multiple cleavage sites.

d. The subunit structure of activated Factor VIII. Factor VIIIa subunits of 92 kDa and 80 kDa are indicated as 92k and 80k, respectively. Their amino terminal and carboxy terminal amino acid positions within the full-length sequence are indicated.

e. The structure of the cDNA and protein of pCLB202 containing a direct fusion between the PstI and BamHI site indicated in b. The resulting protein is indicated containing a peptide bond between Ala-867 and Asp-1563. The total length of the protein is 1637 amino acids. (The landmarks of the repeat border positions and specific proteolytic cleavage sites are as depicted; see above.)

f. The structure of the cDNA and protein pCLB203 containing a MluI-linker sequence coding for four extra amino acids that bridge the MaeIII site and HgiAI site, as indicated under b. The total length of the protein is 1411 amino acids. (The landmarks of the repeat border positions and specific proteolytic cleavage sites are depicted; see above.)

g. The structure of the cDNA and protein of the deletion mutant pCLB204. Using loop-out mutagenesis Val-374 is linked to Gln-1638. The thrombin proteolytic cleavage site at Arg-372 is indicated. The total length of the protein is 1069 amino acids.

Figure 4:
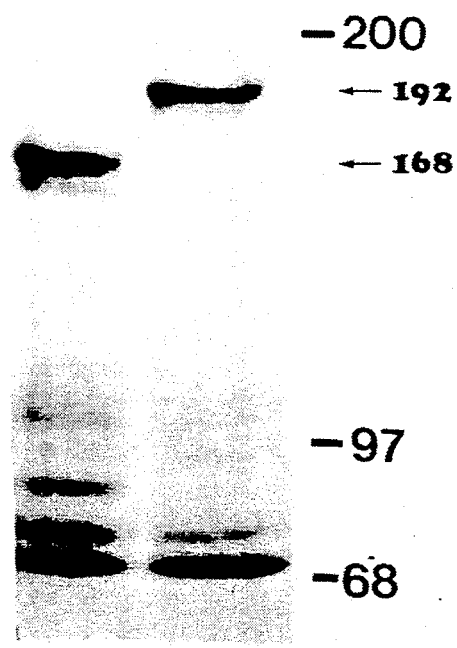

FIG. 4 shows the results of a molecular weight (size) determination of several deletion mutant Factor VIII proteins using immunoprecipitation and electrophoresis. In lane 1 of the autoradiograph is the protein made with vector pCLB203 and in lane 2 the protein made with the vector pCLB202. The molecular weight markers are as indicated.

DESCRIPTION OF THE SPECIFIC EMBODIMENTS

In accordance with the subject invention, novel DNA constructs and novel compositions comprising host cells producing polypeptides having Factor VIII activity are provided. The polypeptides having Factor VIII activity include deletion mutant proteins of Factor VIII in which substantially all of the central region or "B domain" as well as a portion of the 92 kiloDalton (kDa) region has been deleted. Plasmid constructs comprising DNA sequences encoding deletion polypeptides having Factor VIII activity are used to transform a host cell. The transformed host cell is then grown to express the gene. The host cell may be either a eukaryotic or a prokaryotic cell.

Human Factor VIII has the sequence shown in FIG. 1. Single letter abbreviations for the amino acids are used, and have the following meaning: A=alanine; R=arginine; N=asparagine; D=aspartic acid; C=cysteine; Q=glutamine; E=glutamic acid; G=glycine; H=histidine; I=isoleucine; L=leucine; K=lysine; M=methionine; F=phenylalanine; P=proline; S=serine; T=threonine; W=tryptophan; Y=tyrosine; and V=valine. The numbering of the amino acid sequence starts with A-1, the first amino acid after the 19 amino acid signal sequence. The last amino acid of Factor VIII is Y-2332. This numbering is used throughout the specification. Factor VIII-like materials, including Factor VIII fragments, mutants of the polypeptide as well as fusion peptides comprising functional portions of Factor VIII having the biological activity of the intact Factor VIII, including blood clotting activity are also provided.

The polypeptides of this invention include congeners of Factor VIII, namely compounds having at least one biological activity of Factor VIII and having at least one amino acid sequence having substantially the same amino acid sequence as Factor VIII. The congener may have a greater or lesser number of amino acids than Factor VIII. Biological activity includes the ability, when administered to patients with Hemophilia A, to correct the clotting defect and/or immunological cross-reactivity with naturally occurring Factor VIII. The correction thus may be effected either by direct action in the clotting cascade or by binding to antibodies against Factor VIII so that the biological activity of subsequently administered Factor VIII is less affected. By "immunological cross-reactivity" is meant that an antibody induced by a novel polypeptide of this invention will cross-react with intact Factor VIII. The polypeptide will have at least one biologically active sequence, for example immunological or epitopic, and may have more than one biologically active sequence, where such sequence may compete with a naturally occurring product for the biological property.

Novel polypeptides of interest will for the most part have a formula comprising an N-terminal region, $N_R$; a linking region, $L_R$; and a C-terminal region, $C_R$. $N_R$ is characterized as having an amino acid sequence substantially corresponding to a consecutive sequence found in amino acid sequence A-1 through R-740 of the full-length Factor VIII (the "A1A2 domain" or 92 kDa polypeptide), wherein no more than about 45%, usually no more than about 20%, preferably no more than about 10%, most preferably no more than about 5% of the amino acids in the A1A2 domain have been deleted. Preferred sequences correspond substantially to the sequences A-1 through D-712, or A-1 through R-740.

$L_R$ may be a short linking group of from 1 to 20 amino acids, a bond or any sequence of amino acids, usually not substantially similar to the sequence of the "B domain" of the full-length Factor VIII protein. It may also comprise sequences corresponding substantially to consecutive sequences in the B domain up to the complete sequence S-741 through S-1637, or any portion thereof. Of particular interest are compositions wherein $L_R$ comprises at least one of the sequences S-741 through A-867 and D-1563 through S-1637.

$C_R$ is characterized as having an amino acid sequence substantially similar to a consecutive sequence found in the sequence of Factor VIII which includes amino acids Q-1638 through Y-2332, wherein no more than about 25%, usually no more than about 20%, preferably no more than about 10% of the amino acids Q-1638 through Y-2332 have been deleted. The sequence preferably includes sequences corresponding substantially to the Factor VIII sequences Q-1638 through Y-2332, E-1649 through Y-2332, S-1669 through Y-2332 and S-1690 through Y-2332, more preferably Q-1638 through Y-2332.

The polypeptides of interest may be fragments of Factor VIII wherein up to about 75% of the amino acids have been deleted from the full length Factor VIII, or fusion proteins wherein the 92 kDa protein or a fragment thereof is fused to the 80 kDa polypeptide or a fragment thereof. The polypeptide usually will have no more than about 75% of the amino acids deleted, usually no more than about 45% of the amino acids deleted, more usually no more than about 40% of the amino acids deleted. Usually the polypeptides of interest will comprise substantially all of the N-terminal and C-terminal amino acids of full length Factor VIII. By N-terminal and C-terminal amino acids is intended at least about 20 amino acids at either terminus.

To provide for immunogenicity, the Factor VIII congeners can be joined covalently to a large immunogenic polypeptide entity. Exemplary of such immunogenic entities are bovine serum albumin, keyhole limpet hemocyanin (KLH) and the like. These conjugated polypeptides will be useful for inducing antibodies in an appropriate host organism. The antibodies can be used to determine the presence or absence and/or concentration of Factor VIII in a bodily fluid, the absence of which may indicate Hemophilia A.

Preparation of Congeners of Factor VIII

Factor VIII congeners may be obtained in a variety of ways. They may be obtained by proteolytic cleavage of the full-length Factor VIII into three regions, preferably by cleavage at R-740 and Q-1638 followed by truncating the amino or carboxyl terminus of the A-1 through R-740 sequence at least one amino acid at a time and/or truncating the amino or carboxyl terminus of the sequence Q-1638 through Y-2332 at least one amino acid at a time. The polypeptide fragments obtained may then be fused directly or via a central linking group, or the fragments may be combined in a composition to provide for Factor VIII activity.

Factor VIII congeners, including fusion proteins in which the $N_R$ and $C_R$ are fused, can also be prepared by recombinant DNA techniques. Techniques used in isolating the Factor VIII gene are known in the art, including synthesis, isolation from genomic DNA, preparation from cDNA, or combinations thereof. The various techniques for manipulation of the genes are well known, and include restriction, digestion, resection, ligation, in vitro mutagenesis, primer repair, and poly linkers and adapters, and the like. See Maniatis et al., *Molecular Cloning*, Cold Spring Harbor Laboratory, Cold Spring Harbor, N.Y., 1982.

Generally the method comprises preparing a genomic library from cells which synthesize Factor VIII. To enhance the likelihood of identifying the correct sequence, a cDNA library from cells which do not produce Factor VIII may be used to cross-hybridize. An assay for the expression of Factor VIII using restriction fragments inserted into a prokaryotic expression vector such as pTZ18 or 19 and screening with antibodies for Factor VIII to detect a cross-reactive peptide fragment or the like can be used.

Once a complete gene has been identified, either as cDNA or chromosomal DNA, the desired modifications in the structural gene can be made in several ways. The modifications may involve deletions, insertions, combinations thereof, as well as substitutions, where the variations may involve as much as about 75% of the molecule. Changes, such as deletions, may involve the internal regions, particularly regions from about base pair 2284 through about base pair 4974 (see FIG. 1 for numbering). Additionally, up to about 45% of the base pairs 5' to base pair 2284 and/or up to about 20% of the base pairs 3' to base pair 4974 may be deleted. Of particular interest are DNA sequences wherein the region encoding mature protein comprises base pairs 64 through 2199 or 2283 joined in reading frame with base pairs 4975, 5008, 5068, or 5131 through 7059.

The cDNA fragments comprising the above base pairs may be used directly, they may be joined together, or additional base pairs may be inserted between the two fragments, including fragments corresponding to all or a portion of base pairs 2284 through 4974. Of particular interest for insertion are at least one of fragments comprising base pairs 2284 to 2664 and 4750 to 4974. Usually the DNA sequences will comprise substantially all of the 5' region from about base pair 64 through about base pair 1071, and substantially all of the 3' region from about base pair 5185 through the end of the open reading frame (base pair 7059).

Deletions may be made in a number of ways known to those skilled in the art, including by enzymatically cutting the full length Factor VIII cDNA followed by modification and ligation of the purified fragments or by site-directed mutagenesis, especially by loop-out mutagenesis as described by Kramer et al., *Nucl. Acids Res.* (1984) 12:9441-9456. The gene thus obtained may then be manipulated in a variety of ways well known in the art to provide for expression.

Both prokaryotic and eukaryotic hosts may be employed, which may include bacteria, yeast, mammalian cells, for example, CHO cells, C127 cells, human "293" cells, myeloma cells, or specialized cells such as liver cells, and COS cells. Therefore where the gene is to be expressed in a host which recognizes the wild-type translational and transcriptional regulatory regions of Factor VIII, the entire gene with its wild-type 5', and 3'-regulatory regions may be introduced into an appropriate expression vector. Various expression vectors exist employing replication systems from mammalian viruses, such as simian virus 40, Epstein-Barr virus, bovine papalloma virus, vaccinia virus, etc.

Where the gene is to be expressed in a host which does not recognize the naturally occurring wild-type transcriptional and translational regulatory regions, further manipulation will be required. Conveniently a variety of 3'-transcriptional regulatory regions are known and may be inserted downstream from the stop codons. The non-coding 5' region upstream from the structural gene may be removed by endonuclease restriction, Bal31 resection, or the like. Alternatively, where a convenient restriction site is present near the 5' terminus of the structural gene, the structural gene may be restricted and an adapter employed for linking the structural gene to the promoter region, where the adapter provides for the lost nucleotides of the structural gene.

Various strategies may be employed for providing a foreign expression cassette, which in the 5'-3'-direction of transcription has a transcriptional regulatory region and a translational initiation region, which may also include regulatory sequences allowing for the induction of regulation; an open reading frame encoding the full length Factor VIII or a congener of Factor VIII including the deletion mutant proteins, desirably including a secretory leader sequence recognized by the proposed host cell; and translational and transcriptional termination regions. The expression cassette may additionally include at least one marker gene. The initiation and termination regions are functional in the host cell, and may be either homologous (derived from the original host), or heterologous (derived from a foreign source) or synthetic DNA sequences. The expression cassette thus may be wholly or partially derived from natural sources, and either wholly or partially derived from sources homologous to the host cell, or heterologous to the host cell. The various DNA constructs (DNA sequences, vectors, plasmids, expression cassettes) of the invention are isolated and/or purified, or synthesized and thus are not "naturally occurring."

For optimal gene expression, the nucleotide sequences surrounding the translational initiation codon ATG have been found to be important in animal cells. For example, Kozak, *Microbiol. Reviews* (1983) 47:1–45, has studied extensively the effect of these regions on the expression of polypeptides such as insulin in COS cells. Thus it may be necessary to modify the nucleotide sequences surrounding the initiation codon. This can be done by site-directed mutagenesis or by fusing the exogenous gene to the initiation region of a highly expressed gene.

Illustrative transcriptional regulatory regions or promoters include; for bacteria, the β-gal promoter, amylase promoter, lambda left and right promoters, trp and lac promoters, trp-lac fusion promoter, etc.; for yeast, glycolytic enzyme promoters, such as ADH-1 -2 promoters, PGK promoter, and lactase promoter, and the like; for mammalian cells, SV40 early and late promoters, cytomegalovirus (CMV) promoter, β-actin promoter, adenovirus major late promoters, and the like.

In eukaryotic cells, regulatory sequences can include, for example, the cytomegalovirus enhancer sequence which can be fused to a promoter sequence such as the SV40 promoter, forming a chimeric promoter, or inserted elsewhere in the expression cassette, preferably in close proximity to the promoter sequence. Expression of the structural gene can also be amplified by, for example, ligating in tandem a gene for a dominant amplifiable genetic marker 5' or 3' to the structural gene and growing the host cells under selective conditions. An example of an amplifiable gene is the gene for dihydrofolate reductase (dhfr), the expression of which may be increased in cells rendered resistant to methotrexate (mtx), a folate antagonist. Of interest for expression in mammalian cells such as COS cells, are expression cassettes capable of expressing Factor VIII or congeners thereof which employ a metallothionein promoter, or the SV40 early transcription unit transcription promoter (SVep), particularly the Rous Sarcoma Virus-Long Terminal Repeat (RSV-LTR) promoter in tandem with the SVep promoter. Examples of promoters and promoter/enhancer combinations which can be used in C127 cells have been described. See, for example, Hurwitz et al., *Nucl. Acids Res.* (1987) 15:7137–7153. For optimal expression, the expression cassette may additionally comprise an intron, preferably in the 5' region of mRNA.

In addition, a fused gene may be prepared by providing a 5'-sequence to the structural gene which encodes a secretory leader and a processing signal. For secretion of Factor VIII polypeptides the naturally occurring Factor VIII leader sequence is preferably used, but other signal sequences including secretory leaders of penicillinase, α-factor, immunoglobulin, T-cell receptors, outer membrane proteins, serum albumin, insulin, tissue plasminogen activator, digestive tract enzymes, and the like may also be used. By fusion of a secretory leader in proper reading frame with a structural gene for Factor VIII or a congener thereof, the mature Factor VIII may be secreted into the culture medium.

The termination region may be derived from the 3' region of the gene from which the initiation region was obtained or from a different gene. A large number of termination regions are known and have been found to be satisfactory in a variety of hosts from the same and different genera and species. The termination region may include sequences for the proper processing of the mRNA in a mammalian cell: i.e., a small intron and a polyadenylation signal.

During the construction of the expression cassette, the various DNA fragments will usually be cloned in an appropriate cloning vector, which allows for expansion of the DNA, modification of the DNA or manipulation by joining or removing of the sequences, linkers, or the like. Normally, the vectors will be capable of replication in at least a relatively high copy number in *E. coli*. A numbers of vectors are readily available for cloning, including such vectors as pBR322, pML2, pUC7-pUC19, pSP64, pSP65, pSP18, pSP19, pTZ18 and pTZ18R, pTZ19 and pTZ19R and the like.

The cloning vectors are characterized as having an efficient origin of replication at least functional in *E. coli*. Also the cloning vector will have at least one unique restriction site, usually a plurality of unique restriction sites and may also include multiple restriction sites, particularly two of the same restriction sites for substitution. In addition, the cloning vector will have one or more markers which provide for selection for transformants. The markers will normally provide for resistance to cytotoxic agents such as antibiotics, heavy metals, toxins or the like, complementation of an auxotrophic host, or immunity to a phage. By appropriate restriction of the vector and cassette, and, as appropriate, modification of the ends, by chewing back or filling in overhangs, to provide for blunt ends, by addition linkers, by tailing, complementary ends can be provided for ligation, and joining of the vector to the expression cassette or a component thereof.

In some instances, a shuttle vector will be employed where the vector is capable of replication in different hosts requiring different replication systems. Preferably a simian virus 40 (SV40) origin of replication is employed which allows the plasmid to be propagated in COS-1, while the Bovine Papilloma Virus (BPV-1) genome is used for the episomal maintenance of expression vectors in C127 cells (see for example Howley et al., *Methods of Enzymology* (1983) 101:387–402).

The expression cassette may be included within a replication system for episomal maintenance in an appropriate cellular host or may be provided without a replication system, where it may become integrated into the host genome. The manner of transformation of the host organism with the various DNA constructs is not critical to this invention. The DNA may be introduced into the host in accordance with known techniques, such as transformation, using calcium phosphate precipitated DNA, electroporation, transfection by contacting the cells with a virus, microinjection of the DNA into cells or the like.

As a host organism, normal primary cells or cell lines derived from cultured primary tissue may be used, as well as microbial cells. The host cell is preferably a mammalian cell line, preferably hamster CHO cells, mouse C127 cells or human "293" cells, but microbial cells, for example yeast, preferably a Kluyveromyces species, or bacteria, preferably a Bacillus species, may also be used.

For stable transformation of a mammalian cell line with the expression vector bearing the Factor VIII congener coding sequence and subsequent amplification of the vector inserted in the host chromosome, Chinese hamster ovary cells (CHO) are especially suitable. Transformation involves transfection of the host cell with the expression vector together with a selectable marker gene such as dhfr or a G418 (neo-) resistance gene or the like, and subsequent integration into the chromosome and selection for stable transformation.

Another method for stable transformation for host cell lines uses expression vectors containing BPV-1 sequences. C127 cells are well suited for this purpose. Transformation involves transfection of the host cell with the expression vector containing BPV-1 sequences. Transformants are recognized by the formation of foci. Stable transformants are established and screened for Factor VIII activity using, for example, the KABI Coatest (see Examples 6 and 7) by standard methods. In contrast, when the expression is carried out in a transient transformation system such as COS-1 cells with pSV2-derived expression vectors, there is no selection step.

Once the structural gene has been introduced into the appropriate host, the host may be grown to express the structural gene. The host cell may be grown to high density in an appropriate medium. Where the promoter is inducible, such as in a prokaryotic system, permissive conditions will then be employed, for example temperature change, exhaustion, or excess of a metabolic product or nutrient, or the like. In a mammalian system, where an amplifiable gene is used in tandem with the structural gene, the appropriate means for amplification will be employed.

Where secretion is provided for, the expression product, either fused or unfused, may be isolated from the growth medium by conventional means. Where secretion is not provided for, the host cells may be harvested and lysed in accordance with conventional methods. The desired product is then isolated and purified by conventional techniques, for example affinity chromatography with immobilized antibodies, chromatography on aminohexyl-sepharose or the mixed polyelectrolyte method.

The recombinant products may be glycosylated or non-glycosylated, having the wild-type or other glycosylation. The amount of glycosylation will depend in part upon the sequence of the particular peptide, as well as the organism in which it is produced. Thus, expression of the product in *E. coli* cells will result in an unglycosylated product, and expression of the product in mammalian cells will result in a product with glycosylation similar to the wild-type peptide.

Uses of Factor VIII Congeners

The subject compounds can be used in a wide variety of ways, both in vivo and in vitro. The subject compounds may be used as the active ingredient of pharmaceutical preparations for treating patients exhibiting symptoms of Hemophilia A. By a pharmaceutical composition is meant any preparation to be administered to mammals. Thus, a pharmaceutical preparation with Factor VIII activity is a preparation which can be administered to a mammal to alleviate symptoms associated with Hemophilia A, the inability to properly clot blood. In preparing the pharmaceutical composition, generally the subject polypeptides are admixed with parenterally acceptable vehicles and other suitable excipients in accordance with procedures known in the art. The pharmaceutical preparations may conveniently be a sterile lyophilized preparation of the subject polypeptide which may be reconstituted by addition of a sterile solution suitable for producing solutions, preferably isotonic with the blood of the recipient. The pharmaceutical preparation may be presented in single-unit or multi-dose containers, for example in sealed ampoules or vials. Their use would be analogous to that of known human Factor VIII polypeptide, appropriately adjusted for potencey. The subject polypeptide may be administered in vivo, for example by injection, intravenously, peritoneally, subcutaneously, or the like.

The subject compounds additionally can be used for making antibodies to the subject compounds, which may find use in vivo or in vitro. The antibodies can be prepared in conventional ways, either by using the subject polypeptide as an immunogen and injecting the polypeptide into a mammalian host, for example mouse, cow, goat, sheep, rabbit, etc., particularly with an adjuvant, for example complete Freunds adjuvant, aluminum hydroxide gel, or the like. The host may then be bled and the blood employed for isolation of polyclonal antibodies, or in the case of the mouse, the peripheral blood lymphocytes or splenic lymphocytes (B cells) employed for fusion with an appropriate myeloma cell to immortalize the chromosomes for monoclonal expression of antibodies specific for the subject compounds.

Either polyclonal or monoclonal antibodies may be prepared, which may then be used for diagnosis or detection of the presence of the subject polypeptide in a sample, such as cells or a physiological fluid, for example blood. Failure to detect the subject polypeptide may indicate the condition of hemophilia A.

Probes comprising sequences complementary to Factor VIII mRNA may also be prepared and used as a diagnostic aid, for example, the presence and/or amount of Factor VIII mRNA in a cell may be used for determining whether the patient is making Factor VIII but has developed antibodies which prevent its activity. A test sample comprising a cell, tissue sample or bodily fluid believed to contain hybridizing sequences can be treated so as to lyse any cells, then treated with a denaturing agent such as guanidine hydrochloride to release single-stranded mRNA. The probe labeled with, for example $^{32}P$ or biotinylated nucleotides, can then be hybridized to the cellular mRNA to form a double-stranded complex which may be detected by means of the label. For some purposes it may be desirable to quantitate the amount of Factor VIII mRNA. This is done by comparing the amount of label detected in reference samples containing known amounts of single-stranded Factor VIII mRNA with the amount of label detected in the test sample.

The following examples are offered by way of illustration and not by way of limitation.

EXPERIMENTAL

General cloning techniques were used as described in Maniatis et al., Molecular Cloning: A Laboratory Manual, Cold Spring Harbor Laboratory, CSH, NY, 1982. All DNA-modifying enzymes were obtained from commercial suppliers. They were used according to manufacturers instructions. Materials and apparatus for DNA purification and separation were used according to instructions from the supplier.

EXAMPLE 1

Figure 2:
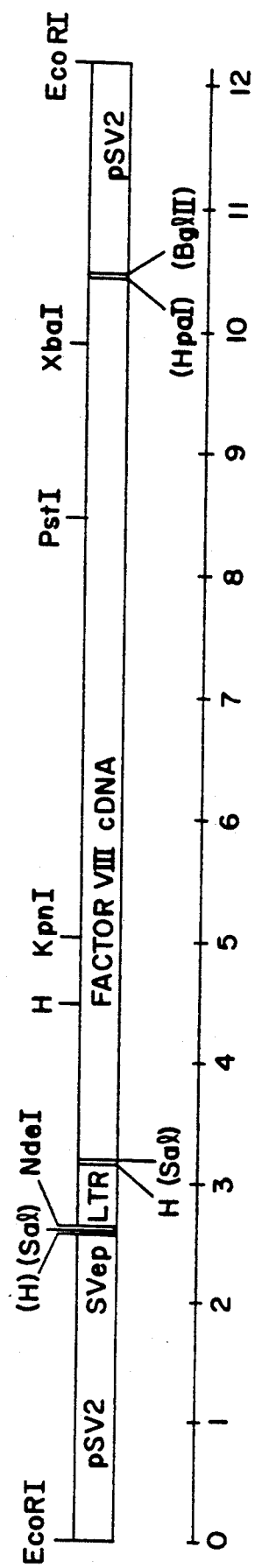
FIG. 2 shows the structure of expression vector pCLB201 encoding the full-length Factor VIII protein. The circular plasmid pCLB201 is shown beginning with the EcoRI position within the 4217 bp HindIII-BglII fragment derived from plasmid pSV2 (Gorman, 1985 *DNA Cloning* (Ed. Glover) IRL Press, pp. 143–169; Mulligan and Berg, *Proc. Natl. Acad. Sci. USA* (1981) 78:2072). The early SV40-promoter region is indicated: SVep. The vector also contains a NdeI-HindIII fragment derived from plasmid pRSV-neo (Gorman (1985) supra) bearing the Rous Sarcoma Virus-Long Terminal Repeat (LTR) inserted into a SalI site. The full-length Factor VIII is encoded by a SalI-HpaI fragment of 7440 bp and indicated: Factor VIII cDNA (H=HindIII, Sal=SalI). The restriction endonuclease cleavage sites lost during construction of pCLB201 are enclosed in parenthesis. The size of the plasmid is given in kilobase pairs (kb).

Construction of Expression Vector pCLB201 pCLB201 is an expression vector comprising the RSV-LTR promoter in the right orientation for transcriptional initiation, and the full-length Factor VIII cDNA (see FIG. 2). It is derived from the pSV2-vector of Mulligan and Berg, Proc. Natl. Acad. Sci. USA (1981) 78:2072.

The unique HindIII site of the plasmid pSV2.tPA (Van Zonneveld et al., Proc. Natl. Acad. Sci. USA (1986) 83:4670-4674) was modified into a SalI site by making blunt the HindIII sticky-ends and ligating to the blunt ends SalI-linkers (5'-CGTCGACG-3'). A plasmid containing a SalI site was selected and identified as pCLB91. This plasmid is the same as pSV2.tPA except that it contains a SalI linker inserted into the HindIII site.

The isolation of Factor VIII mRNA from human liver, and the preparation, purification and identification of its cDNA and its assembly in the plasmid pEP121 resulting in plasmid pCLB89 have been described in patent application EP 0253455, which disclosure is hereby incorporated by reference. A 7440 bp long SalI-HpaI fragment from pCLB89 containing the Factor VIII cDNA (see FIG. 1) was purified and inserted into pCLB91 digested wth SalI and BglII. The resulting expression vector pCLB200 contained an intact SalI site with the HpaI site ligated to the BglII site which had been filled in.

Plasmid pRSVneo (Gorman, DNA Cloning, 1985, ed., D. Glover, IRL-press, Washington, Oxford, pp. 143-169) was digested with NdeI and HindIII and incubated with the Klenow fragment of DNA polymerase to create blunt ends and the 0.6 kb fragment containing a Rous Sarcoma Virus-Long Terminal Repeat (RSV-LTR) sequence was isolated and inserted into the SalI site of pCLB200 which had similarly been made blunt-ended to form expression vector pCLB201 (see FIG. 2).

EXAMPLE 2

Construction of pCLB202

A deletion mutant of Factor VIII having a deletion from the PstI site at nucleotide sequence position 2660 (see FIG. 3b) to the BamHI site at position 4749 (see FIG. 3b), was constructed in plasmid pGB860 as described in patent application EP 0253455. The Factor VIII DNA in pGB860 has a deletion of the DNA coding for 695 amino acids in the central region.

Figures 3A, 3B, 3C, 3D, 3E, 3F, 3G:
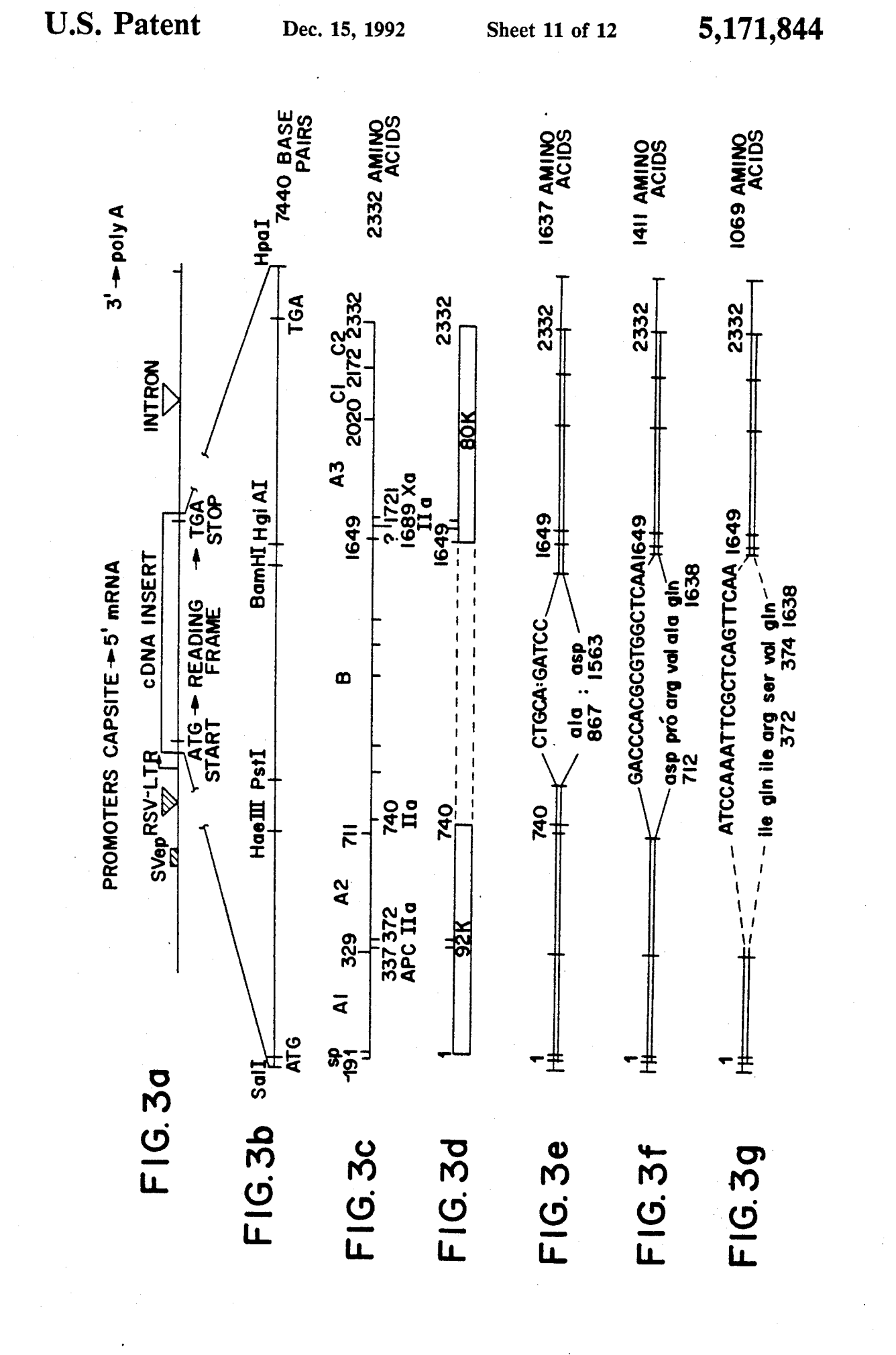

Expression vector pCLB202 was derived from pGB860 and pCLB201. Both plasmids were digested with KpnI and XbaI restriction enzymes. The 3.1 kb KpnI-XbaI fragment in pGB860 was ligated to the 7 kb KpnI-XbaI fragment from pCLB201. The resulting plasmid pCLB202 has intact KpnI and XbaI sites. Its structure is depicted in FIG. 3e.

EXAMPLE 3

Construction of pCLB203

A. pCLB100

The SalI-HpaI 7440 bp fragment (see FIG. 2) from pCLB89 was inserted into plasmid pSP64 (Melton et al., Nucleic Acids Res. (1984) 12:7035-7056) which had been cleaved with SalI and SmaI. The resulting plasmid, pCLB100, contained an intact SalI-site and the HpaI-end linked to the SmaI-end.

B. pCLB101: (numbers in parentheses refer to FIG. 1)

(1) Plasmid pCLB100 was digested with KpnI and TthIIII, generating a 631 bp fragment: KpnI(1817)-TthIIII(2447). The 631 bp fragment was purified, then cut with MaeIII(2199). The MaeIII sticky end was filled in resulting in a 383 bp fragment.

(2) Plasmid pCLB100 was digested with ApaI and BanI. The 669 bp ApaI(6200)-BanI(5532) fragment was isolated.

(3) Plasmid pCLB100 was digested with HgiAI, producing a HgiAI-fragment of 634 bp. The fragment incubated with T4 DNA polymerase to make blunt ends, then digested with BanI, to produce a 565 bp fragment.

(4) Plasmid pCLB100 was digested with ApaI and KpnI, generating a 5.9 kb long fragment (ApaI(6200)-KpnI(1817)) containing vector sequences for maintenance and propagation in E. coli.

(5) The fragments obtained in Steps (1) through (4) were purified and equimolar amounts of the fragments and a ten-fold molar excess of MluI-linker (CCACGCGTGG) were ligated, giving rise to plasmid pCLB101. Plasmid pCLB101 contained a MluI-linker between the MaeIII and HgiAI-sites (see FIG. 3b) in addition to KpnI, BanI and ApaI sites. Four extra amino acids (P-R-V-A) between amino acids D-712 and Q-1638 (FIG. 1) are shown in FIG. 3f.

(c) pCLB203:

pCLB101 and pCLB201 were digested with enzymes KpnI and XbaI. The 2.4 kb KpnI-XbaI fragment from pCLB101 was ligated to the 7.0 kb KpnI-XbaI fragment derived from pCLB201. The resulting plasmid pCLB203 possessed intact KpnI and XbaI sites. Its structure is depicted in FIG. 3f.

EXAMPLE 4

Construction of pCLB212 pCLB212 was constructed using the loop-out mutagenesis technique as described in Kramer et al., Nucleic Acids Res. (1984) 12:9441-9456. The deletion mutagenesis of the central region of Factor VIII cDNA was performed using the following oligonucleotide:

Primer IV
3' TCC.CAA.AGA.TCA.ACA.CTG.GTT.TTG.GGT.GGT.CAG.AAC 5' to produce in Factor VIII cDNA internal deletion of the sequences coding for amino acids K-713 through S-1637.

The corresponding protein contains an internal deletion of 925 amino acid residues compared with the full length Factor VIII protein.

To obtain a target fragment for loop-out mutagenesis a HindIII-PstI fragment of 1.4 kb derived from pCLB203 (Example 3) was selected. The nucleotide position (FIG. 1) of the HindIII-site is at 1025 in the full length Factor VIII sequence upstream of the region to be modified, the PstI site is at position 5165 downstream of the region. These sites are indicated in FIG. 2. The 1.4 kb fragment was subcloned in M13mp9 followed by the loop-out mutagenesis. After selecting the fragment with the precise deletion, this was followed by the insertion of the KpnI-PstI part of the HindIII-PstI fragment containing the desired deletion into an appropriate expression vector by preparing fragments with sticky, unique restriction enzyme ends (numbers refer to FIG. 1), according to the following steps:

(1) For the expression of the mutant Factor VIII molecules a new plasmid pCLB211 was constructed. The SalI-HpaI fragment of 7440 bp (FIG. 1) derived from pCLB89 was inserted into the expression vector pSVL (Pharmacia, No. 27-4509-01, Uppsala, Sweden) enabling transcription from a late SV40 promoter in mammalian cells. The plasmid pSVL was cleaved with XhoI and SmaI. The resulting plasmid pCLB211 contains an XhoI end linked to the SalI end, since both 5' protruding ends of these enzymes are identical, and the SmaI end linked to the HpaI end.

(2) Plasmid pCLB211 was digested with ApaI and SalI. The 1.4 kb ApaI(6200)-SalI(unique in pSVL-part of pCLB211) fragment was isolated.

(3) Plasmid pCLB100 was digested with NdeI, PstI and ApaI. Two fragments were isolated: a PstI(5165)-NdeI(5527) fragment of 363 bp and second fragment, NdeI(5527)-ApaI(6200) of 674 bp.

(4) Plasmid pCLB100 was digested with KpnI and SacI. A KpnI(1817)-SacI(19) of 1799 bp was isolated.

(5) Plasmid pCLB211 was digested with SalI and SacI. A 4.5 kb SalI(unique in the pSVL vector)-SacI(19) fragment was obtained.

(6) An M13-bacteriophage containing a HindIII(1025)-PstI(5165) fragment with the desired deletion as verified with sequence analysis, was digested with KpnI and PstI. A 584 bp PstI(5165)-KpnI(1819) fragment was isolated.

(7) The six isolated fragments from steps (2) through (6) were mixed in equimolar amounts and ligated. A plasmid containing all six fragments was selected. The plasmid pCLB212 expressed the exemplary compound 3b (Table II). The compound 3b differs from compound 3 (illustrated in FIG. 3f) as it is missing the MluI linker and corresponding four amino acids.

EXAMPLE 5

Construction of pCLB208, pCLB209 and pCLB210 pCLB208, pCLB209 and pCLB210 were constructed using the loop-out mutagenesis technique as described in Kramer et al., *Nucleic Acids Res.* (1984) 12:9441-9456.

A. Loop-out Mutagenesis

Deletion mutagenesis of the central region of Factor VIII cDNA was performed using the following oligonucleotides:

Primer I:
3' TTA.CGG.TAA.CTT.GGT.TCT.CTT.TAT.TGA.GCA.TGA.TGA 5'

Primer II:
3' TTA.CGG.TAA.CTT.GGT.TCT.AGT.CAA.CTT.TAC.TTC.TTC 5'

Primer III:
3' TTA.CGG.TAA.CTT.GGT.TCT.TCG.AAA.GTT.TTC.TTT.TGT 5' to produce internal deletions in Factor VIII cDNA of the sequences coding for amino acids S-741 through R-1648 (Primer I), S-741 through I-1668 (Primer II), and S-741 through R-1689 (Primer III). The corresponding proteins contain internal deletions of 908 (I), 928 (II) and 949 (III) amino acid residues, respectively.

B. Preparation of Target Fragments

To obtain a target fragment for loop-out mutagenesis a fragment of 0.8 kb derived from pCLB101 was constructed as follows.

Plasmid pCLB101 was digested with EcoRI, the EcoRI sites were filled in and a further digestion with KpnI followed. A 479 bp KpnI(1819)-EcoRI(2297) fragment (the numbers of nucleotide positions are as described in FIG. 1) was isolated. Plasmid pCLB101 was digested with BamHI; the sticky ends were filled in and a further digestion with PstI followed. A 416 bp BamHI(4749)-PstI(5165) fragment was isolated. These fragments were ligated in equimolar amounts and subcloned in M13mp19 amber. The M13 bacteriophage containing a KpnI-PstI fragment of 895 bp from 1819 upstream from the region to be modified to 5165 downstream from that region and with a large deletion in the Factor VIII coding sequence was selected for the loop out mutagenesis. After selecting the fragment with the precise deletion obtained with Primer I, II, or III in bacteriophage M13, the KpnI-PstI fragment containing the desired deletion was inserted into an appropriate expression vector derived from pCLB211 (see Example 4) using the following steps and preparing fragments with sticky, unique restriction enzyme ends (numbers refer to FIG. 1):

(1) Plasmid pCLB211 was digested with ApaI and SalI. The 1.4 kb ApaI(6200)-SalI (unique in pSVL-part of pCLB211) fragment was isolated.

(2) From plasmid pCLB100 digested with NdeI, PstI and ApaI a 363 bp PstI(5165)-NdeI(5527) fragment and a 674 bp NdeI(5527)-ApaI(6200) fragment were isolated.

(3) Plasmid pCLB100 was digested with KpnI and SacI and a 1799 bp KpnI(1817)-SacI(19) fragment isolated.

(4) Plasmid pCLB211 was digested with SalI and SacI. The 4.5 kb SalI(unique in the pSVL vector)-SacI(19) fragment was isolated.

(5) The M13 bacteriophage containing the fragment with the desired mutation was digested with KpnI and PstI. The KpnI-PstI fragments containing the desired mutation were isolated for all three mutageneses.

C. Final Construction

The six fragments from (1) to (5) above were isolated (by hybridization and restriction enzyme digestion), mixed in equimolar amounts and ligated. Plasmids containing all of the desired fragments were selected. Using Primers I, II, or III shown above, three new expression vectors were constructed for the expression of the exemplary compound described in Table I:
1. pCLB208 for compound 7 with Primer I;
2. pCLB209 for compound 8 with Primer II; and
3. pCLB210 for compound 9 with Primer III.

tioned medium after harvesting. To inhibit protein glycosylation, tunicamycin can be added to the conditioned medium (final concentration 0.001 mg/ml). Conditioned media were harvested 4 days after transfection; produced proteins were assayed.

B. Biological Activity of Recombinant Factor VIII

The conditioned medium was assayed for Factor

TABLE I

Deletion Mutant Factor VIII Proteins

| Compound | $N_R$ | $N_R$ Del.‡ | $L_R$ | $L_R$ Del.‡ | $C_R$ | $C_R$ Del.‡ | Expression Vector |
|---|---|---|---|---|---|---|---|
| 1. | A-1 → R-740 | 0 | S-741 → S-1637 | 0 | Q-1638 → Y-2332 | 0 | pCLB201 |
| 2. | A-1 → R-740 | 0 | S-741 → A-867 + D-1563 → S1637 | 695 | Q-1638 → Y-2332 | 0 | pCLB202 |
| 3. | A-1 → D-712 | 28 | P-R-V-A | 897 | Q-1638 → Y-2332 | 0 | pCLB203 |
| 3b. | A-1 → D-712 | 28 | peptide bond | 897 | Q-1638 → Y-2332 | 0 | pCLB212 |
| 4. | A-1 → V-374 | 366 | peptide bond | 897 | Q-1638 → Y-2332 | 0 | pCLB204 |
| 7. | A-1 → R-740 | 0 | peptide bond | 897 | E-1649 → Y-2332 | 11 | pCLB208 |
| 8. | A-1 → R-740 | 0 | peptide bond | 897 | S-1649 → Y-2332 | 31 | pCLB209 |
| 9. | A-1 → R-740 | 0 | peptide bond | 897 | S-1690 → Y-2332 | 52 | pCLB210 |

→ means an uninterrupted sequence of Factor VIII amino acids
‡The number of deleted amino acids in each region compared with full-length Factor VIII are listed in the respective columns with the heading Del. The numbering of the amino acids is as used in FIG. 1.

EXAMPLE 6

Transient Expression of Recombinant Factor VIII DNA and Assay of Produced Proteins A. Transfection of COS-1 Cells and Metabolic Labeling The expression vectors obtained according to the previous examples were introduced into COS-1 cells using a DEAE transfection technique. Vector DNA was precipitated by incubating with DEAE-dextran for 2 hrs, followed by treatment with chloroquine shock for 2 hrs, as described by Lopata et al., *Nucleic Acids Res.* (1984) 12:5707 and Luthman and Magnusson, *Nucleic Acids Res.* (1983) 11: 1295. The medium used for growth of the COS-1 cells and also for the conditioned medium was Iscove's DMEM (Flow) supplemented with 10% (v/v) heat inactivated fetal calf serum (Flow). The medium was changed 48 hrs after transfection. The conditioned medium was collected 48 hrs later.

Metabolic labeling of the proteins in the transfected cells was carried out using serum free RPMI-medium (Gibco). Two days after transfection, transfectants were incubated for 4 hrs with 50 μCi/ml L-$^{35}$S-methionine (Amersham, 1985; 370 MBeq/330 μl; specific activity: over 100 Ci/mMole), followed by an overnight incubation with 1 mM L-methionine before harvesting the conditioned medium. In order to suppress protein degradation, protease inhibitors such as phenyl methane sulphonyl fluoride (PMSF) were added to the condi- VIII activity using (1) the standard coagulation or clotting assay and (2) the chromogenic activity assay (Kabi Coatest).

The standard coagulation or clotting assay (so-called activated partial thromboplastin time) was performed using hemophilia plasma as described by Veldkamp et al., *Thromb. Diath. Haemorrh.* (1968) 19:279. The conditioned medium was citrated before examination.

The chromogenic activity or Kabi Coatest assay was performed according to procedures supplied by the manufacturer Kabi-Vitrum, except that all volumes prescribed were divided by four and 25 μl of conditioned medium was tested. The Factor VIII-like proteins were activated for 15 min, at which time the chromogenic substrate (S2222) was added.

Inhibition of Factor VIII activity was measured according to the standard Bethesda protocol (Kasper et al., *Thromb. Diath. Haemorrh.* (1975) 34:869–871. The immunoglobulins used were purified by ion exchange and protein A Sepharose chromatography prior to use.

The standard for biological activity assays for Factor VIII was a pool of citrated plasma (0.5 mM final conc.) which was assumed to contain 1 U of Factor VIII activity or antigen per ml.

The biological activity for various of the deletion proteins are shown in Table II. Mutant proteins with deletions exhibited Factor VIII clotting activity.

TABLE II

Factor VIII Activity and Protein Amounts

| Comp.[1] | Length in Amino Acids | (Deletion) | Factor VIII Activity (mU/ml)[7] | | Residual Activity After Addition of Antibodies[2] | | Antigen Determin. |
|---|---|---|---|---|---|---|---|
| | | | Chrom Assay[2] | Stand Assay[3] | CLB.CAgA[4] | Pat. J[5] | |
| 1 | 2332 | 10(0) | 1.0 | —[6] | —[6] | —[6] | >5 mU |
| 2 | 1637 | (695) | 6.7 | 2 | 1% | 1% | 7 mU |
| 3 | 1411 | (925) | 17.3 | 5 | 2% | 1% | 20 mU |
| 3b | 1407 | (925) | 15.0 | NT[9] | NT[9] | NT[9] | 20 mU |
| 4 | 1069 | (1263) | ND[10] | ND[10] | ND[10] | ND[10] | ND[10] |
| 7 | 1424 | (908) | 15.0 | NT[9] | NT[9] | NT[9] | NT[9] |
| 8 | 1404 | (928) | 15.0 | NT[9] | NT[9] | NT[9] | NT[9] |
| 9 | 1383 | (949) | ND[10] | NT[9] | NT[9] | NT[9] | NT[9] |

TABLE II-continued

| | | Factor VIII Activity and Protein Amounts | | | | |
|---|---|---|---|---|---|---|
| | | Factor VIII Activity (mU/ml)[7] | | Residual Activity After Addition of Antibodies[2] | | Antigen |
| Comp.[1] | Length (Deletion) in Amino Acids | Chrom Assay[2] | Stand Assay[3] | CLB.CAgA[4] | Pat. J[5] | Determin. |
| mock (pSV2) | | 0.0 | 0 | | | 0 |

[1]See Table 1.
[2]According to chromogenic (Kabi Coatest) assay.
[3]Standard Clotting assay.
[4]CLB.CAgA, monoclonal antibody to Factor VIII (Stel, Ph.D. thesis (1984) infra).
[5]Inhibitor isolated from serum of patient J.
[6]Initial Activity too low to distinguish possible inactivation.
[7]Conditioned media after 48 hrs incubation. One unit (U) Factor VIII corresponds to 100 ng Factor VIII protein.
[8]Enzyme-linked immunosorbent assay (ELISA).
[9]NT = not tested.
[10]ND = not detectable.

In addition, the established activity of the recombinant protein solution appeared to be inhibited following addition of antibodies known to be inhibitors of plasma-derived Factor VIII activity and/or of so-called inhibitor-sera, obtained from patients with inhibitors, i.e., antibodies against Factor VIII, in their blood.

C. Immunologic Cross-reactivity with Factor VIII (1) Preparation of monoclonal antibodies Balb/c mice were immunized with purified human Factor VIII-von Willebrand factor complex obtained by agarose gel filtration of cryoprecipitate or a Factor VIII concentrate used for therapeutical purposes (Central Laboratory of the Netherlands Red Cross Blood Transfusion Service, Amsterdam, The Netherlands). Van Mourik and Mochtar, *Biochim. Biophys. Acta* (1970) 221:677-679. Lymphocyte hybridization was performed as described by Galfre et al., *Nature* (1977) 266:550-552. Description of the techniques used for selection of clones producing monoclonal antibodies to Factor VIII has been provided elsewhere (Stel, 1984, Ph.D. thesis, University of Amsterdam, The Netherlands). Monoclonal antibodies to Factor VIII were identified according to their reactivity with Factor VIII polypeptides as described in European patent application EP 0253455.

(2) Polyclonal Antibodies to Factor VIII polypeptides

Rabbits were immunized by standard procedures with a Factor VIII preparation which had been purified by chromatography (Stel, supra). The antibodies thus obtained were identified by immunoblotting, as described in European patent application EP 0253455, using purified Factor VIII-von Willebrand factor or purified polypeptides. The antibodies were isolated by polyacrylamide gel electrophoresis then transferred to nitrocellulose sheets as target proteins. Three distinct polyclonal antisera were obtained: RH 63271, RH 63272 and RH 63275. The antisera reacted with the 80 kDa doublet, 92 kDa polypeptide and larger polypeptides. These antisera also reacted with smaller fragments of Factor VIII.

3. ELISA

An ELISA (Enzyme Linked ImmunoSorbent Assay) was used to detect Factor VIII antigen in the conditioned medium. The method is as follows. The ELISA plates were coated by adding 200 µl/well of an appropriate dilution of the Factor VIII specific monoclonal antibody CLB.CAgA (5 mg/l) in 0.05M carbonate buffer, pH 9.8. The plates were sealed and incubated overnight at 4° C. Between all incubations the plates were washed three times with PBS containing 0.05% Tween-20, which was left on the plates for at least one minute.

A series of dilutions of test samples or normal plasma was pipetted into the wells (200 µl/well) in duplicate. The plates were sealed and incubated at 37° C. for 2 hrs without stirring, then washed as described above. For dilution of the antigen a buffer was used which contained 50 mM Tris-HCl buffer, 2% bovine sserum albumin and 1.0M sodium chloride, pH 7.4.

CLB.CAg117-horse radish peroxidase conjugates were diluted approximately 10,000-fold (depending on the sensitivity required) in a buffer containing 50 mM Tris-HCl buffer, 0.2% Tween-20 and 1.0M sodium chloride, pH 7.4. Of this dilution, 200 µl was added to each well, the plates were sealed and incubated for 2 hrs at 37° C. in the dark.

After washing the plates as described above, 150 µl of a freshly prepared solution of tetramethylbenzidine (TMB) (0.1 g/l) and hydrogen peroxide (0.006%) in 0.1M acetate/citric acid buffer, pH 5.5 was added to each well. The plates were incubated for 30 min in the dark at room temperature. The enzyme reaction was stopped by the addition of 150 µl 2N sulphuric acid. Adsorption was determined at 450 nm with an ELISA microreader. As shown in Table II, there was an increase in Factor VIII activity of successive conditioned medium which was approximately proportional to the increase in the amount of Factor VIII proteins in the medium.

D. Size Determination

The size of the produced Factor VIII proteins was established using gel electrophoresis as follows.

The monoclonal and polyclonal sera raised against plasma-derived Factor VIII were used for immunoprecipitation. The antibodies were immobilized on protein A-Sepharose (15 µl serum per 10 mg protein A-Sepharose), then incubated with the metabolically labeled recombinant Factor VIII-like compounds. The immobilized recombinant proteins were reduced using 10% β-mercaptoethanol, then separated on a 5% polyacrylamide SDS gel electrophoresis system (Laemmli, *Nature* (1972) 227:680-685). As shown in FIG. 4 and Table III, the recombinant Factor VIII-like proteins have the size expected for glycosylated proteins. The smaller bands were also present in the control lane.

Based upon the results presented in Table III it can also be concluded that the recombinant Factor VIII-like proteins of the subject invention are glycosylated, since there is a significant difference between the size of the proteins formed in medium with and without tunicamycin, a known inhibitor of asparagine-linked glycosylation.

TABLE III

Size of Secreted Factor VIII Proteins

| Compound[1] | Expression Vector | Length[2] | Deletion[3] | Size[4] | Calculated Established Size[5] | Glycosylation Inhibition[6] |
|---|---|---|---|---|---|---|
| 1 | pCLB201 | 2332 | 0 | 265 kDa | | |
| 2 | pCLB202 | 1637 | 695 | 188 kDa | 192 kDa | 185 kDa |
| 3 | pCLB203 | 1411 | 925 | 162 kDa | 168 kDa | 158 kDa |
| 3b | pCLB212 | 1407 | 925 | 162 kDa | 168 kDa | |
| 4 | pCLB204 | 1069 | 1263 | 123 kDa | 135 kDa | |

[1] See Table I.
[2] The length is the total number of amino acids in the Factor VIII coding sequence of the expression vector.
[3] Deletion means the number of amino acids deleted from the coding sequence of the full-length Factor VIII in the corresponding expression vector.
[4] The size in kilodalton determined on basis of the known amino acid composition.
[5] The size in kilodalton determined by immunoprecipitation of labeled protein followed by electrophoresis.
[6] The size in kilodalton of proteins from cells grown in a medium containing tunicamycin (0.001 mg/ml).

EXAMPLE 7

Construction of Stable Cell Lines Producing Proteins with Factor VIII Activity

A. Expression in CHO Cells

Plasmids pCLB203, 10 μg, and pAdD26SV(A)-3, 1 μg (Kaufman and Sharp, Mol. Cell Biol. (1982) 2:1304–1319), were introduced into dhfr-deficient CHO cells (Chasin and Urlaub, Proc. Natl. Acad. Sci. USA (1980) 77:4216–4220) using the calcium phosphate precipitation technique (Graham and Van der Eb, Virology (1973) 52:456–467). Amplification of Factor VIII and dhfr coding sequences was achieved by stepwise administration of increasing concentrations of methotrexate (mtx) as described by Kaufman and Sharp, J. Mol. Biol. (1982) 159:601–621. Independent transformants resistant to 200 nM mtx were picked and established as stable cell lines. Several of these cell lines produced about 75 mU of Factor VIII activity/ml of culture medium. The amount of Factor VIII activity secreted into the culture medium could be further raised by further amplification of the Factor VIII coding sequences, using mtx in increasing concentrations.

B. Expression in C127 Cells

As described above, expression vectors may be introduced into eukaryote cells, where they integrate into the genome of the host cell. Subsequently the expression cassettes may be amplified. An alternative to integration of the expression vector is its stable maintenance as an episome. An example of the latter is the expression of one of the "mutant". Factor VIII proteins using the episomal BPV-system (Howley et al., Meth. Enzymol. (1983) 101:387–402). The BPV-1 genome (BamHI cleaved) was first introduced into a BamHI cleaved derivative of pTZ18R (Pharmacia) which contains XhoI sites on both sites of the BamHI site. Subsequently the resulting pTZ-BPV plasmid was cleaved using XhoI, yielding a 2.9 kb pTZ fragment and an 8 kb BPV-fragment with XhoI protruding ends. The latter fragment was ligated into plasmid pCLB212 which had been cleaved at its unique SalI site (at position 2040 in the original pSVL vector). The resulting expression vector pGB881 contains the SV40 late promoter, Factor VIII cDNA coding sequence lacking 2775 bp (mainly of the B-domain) and SV40 late polyadenylation signal. Due to the presence of the BPV-genome this vector can be maintained as an episome in the proper host cells, such as mouse C127 cells. Plasmid pGB881 (10 μg) was transfected into C127 cells using the calcium phosphate precipitation technique (Graham and Van der Eb, supra). Foci were isolated 14 days after transfection and subsequently stable cell lines were established. Several cell lines produced 40 mU of Factor VIII activity/ml of culture medium.

EXAMPLE 8

Construction of pCLB204 pCLB204 was constructed using the loop-out mutagenesis techniques described in Kramer et al. (1984) supra. The deletion mutagenesis of the central region of Factor VIII cDNA was performed using the following oligonucleotide:

Primer V
3' TAG.GTT.TAA.GCG.AGT.CAA.GTT.TTG.GGT.GGT.CAG.AAC 5' to produce in Factor VIII cDNA internal deletions of the sequences coding for amino acids A-375 through S-1637 (Primer V). The corresponding protein contains an internal deletion of 1263 amino acids.

To obtain a target fragment for loop-out mutagenesis a HindIII-PstI fragment of 1.4 kb derived from pCLB203 (Example 3) was selected. The nucleotide position of the Hind-III site is at 1025 (see FIG. 1) in the full-length Factor VIII sequence upstream of the region to be modified; the PstI site is at position 5165 downstream. These sites are indicated in FIG. 2. The 1.4 kb fragment was subcloned into M13mp9 followed by loop-out mutagenesis. After selecting the fragment with the precise deletion obtained with Primer V in bacteriophage M13, the HindIII-PstI fragment containing the desired deletion was inserted into an appropriate expression vector derived from pCLB201, using the following steps. Fragments with sticky, unique restriction enzyme ends (numbers refer to FIG. 1) were prepared.

(1) Plasmid pCLB201 was digested with AvaI and XbaI, generating a vector fragment AvaI (737) through XbaI (6951) of about 6 kb.

(2) Plasmid pCLB201 was digested with AvaI and HindIII to give a 289 bp long fragment AvaI (737) through HindIII (1025).

(3) Plasmid pCLB201 was digested with PstI and NdeI to give a PstI (5165) through NdeI (5527) fragment of 363 bp.

(4) Plasmid pCLB201 was digested with NdeI and XbaI to give 1425 bp fragment NdeI (5527) through XbaI (6951).

(5) The M13 bacteriophage containing the fragment with the desired mutations was digested with HindIII and PstI.

(6) The five fragments obtained in (1) through (5) above were isolated, mixed in equimolar amounts and ligated. Plasmids containing all five fragments were selected. Using Primer V, shown above, a new expression vector pCLB204 was constructed for the expression of the exemplary compound 4 described in Table I.

The DNA constructs and methods of the present invention provide a means for preparing polypeptides having Factor VIII activity by introducing a deletion mutant gene encoding a Factor VIII congener into a host cell. The subject compositions find use for treatment of the symptoms of hemophilia A.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A protein characterized as (1) having biological activity of factor VIII, (2) capable of binding von Willebrand factor and (3) having an amino acid sequence represented by the formula:

$$N_R\text{-}l_R\text{-}C_R$$

wherein:
$N_R$ consists essentially of amino acids 1 through 712 of said factor VIII;
$L_R$ consists essentially of P-R-V-A; and
$C_R$ consists essentially of amino acids 1638 through 2332 of factor VIII.

* * * * *

UNITED STATES PATENT AND TRADEMARK OFFICE
CERTIFICATE OF CORRECTION

PATENT NO. : 5,171,844

DATED : December 15, 1992

INVENTOR(S) : van Ooyen, Albert J.J., et al.

It is certified that error appears in the above-identified patent and that said Letters Patent is hereby corrected as shown below:

Column 15, line 20, (Table I), for compound 8 replace "S-1649" with --S-1669--.

Column 16, line 62 (Table II), for compound 1 replace ">5 mU" with --<5 mU--.

Column 22, line 18, in Claim 1 the formula should appear as follows:
--$N_R-L_R-C_R$--.

Signed and Sealed this

Sixth Day of September, 1994

Attest:

Attesting Officer

BRUCE LEHMAN

Commissioner of Patents and Trademarks